US011000223B2

(12) United States Patent
Ser et al.

(10) Patent No.: US 11,000,223 B2
(45) Date of Patent: May 11, 2021

(54) METHODS FOR DETECTING A SLEEP DISORDER AND SLEEP DISORDER DETECTION DEVICES

(71) Applicant: NANYANG TECHNOLOGICAL UNIVERSITY, Singapore (SG)

(72) Inventors: Wee Ser, Singapore (SG); Jianmin Zhang, Singapore (SG); Jufeng Yu, Singapore (SG)

(73) Assignee: Nanyang Technological University, Singapore (SG)

( * ) Notice: Subject to any disclaimer, the term of this patent is extended or adjusted under 35 U.S.C. 154(b) by 278 days.

(21) Appl. No.: 16/075,041

(22) PCT Filed: Feb. 3, 2017

(86) PCT No.: PCT/SG2017/050052
§ 371 (c)(1),
(2) Date: Aug. 2, 2018

(87) PCT Pub. No.: WO2017/135899
PCT Pub. Date: Aug. 10, 2017

(65) Prior Publication Data
US 2019/0038216 A1    Feb. 7, 2019

(30) Foreign Application Priority Data

Feb. 3, 2016  (SG) .......................... 10201600847R

(51) Int. Cl.
*A61B 5/00*  (2006.01)
*A61B 7/00*  (2006.01)
*G06F 16/00*  (2019.01)
*G16H 50/20*  (2018.01)

(52) U.S. Cl.
CPC .......... *A61B 5/4818* (2013.01); *A61B 5/6801* (2013.01); *A61B 7/003* (2013.01); *G06F 16/00* (2019.01); *G16H 50/20* (2018.01); *A61B 5/0004* (2013.01)

(58) Field of Classification Search
None
See application file for complete search history.

(56) References Cited

U.S. PATENT DOCUMENTS 9,629,582 B2 *   4/2017  Ishikawa ................ A61B 7/003
2008/0243014 A1  10/2008 Moussavi et al.
2009/0234241 A1   9/2009 Ota et al.
(Continued)

OTHER PUBLICATIONS

Ankişhan et al., "Comparison of SVM and ANFIS for Snore Related Sounds Classification by Using the Largest Lyapunov Exponent and Entropy," *Comput. Math. Methods Med.*2013:238937, 2013. (14 Pages).
Ben-Israel et. al., "Obstructive Apnea Hypopnea Index Estimation by Analysis of Nocturnal Snoring Signals in Adults," *SLEEP* 35(9):1299-1305, 2012. (10 Pages).
(Continued)

*Primary Examiner* — Kaylee R Wilson
*Assistant Examiner* — Jay B Shah
(74) *Attorney, Agent, or Firm* — Seed IP Law Group LLP

(57) ABSTRACT

According to various embodiments, there is provided a method for detecting a sleep disorder, the method including: processing an audio signal, the audio signal including breathing sounds made by a subject when the subject is asleep; identifying intervals of the audio signal where breathing sounds are absent; and detecting the sleep disorder based on the identified intervals.

19 Claims, 12 Drawing Sheets

(56) References Cited

U.S. PATENT DOCUMENTS

| | | | |
|---|---|---|---|
| 2011/0184302 A1 | 7/2011 | Eschler et al. | |
| 2012/0190996 A1 | 7/2012 | Tanaka et al. | |
| 2013/0261485 A1 | 10/2013 | Ishikawa et al. | |
| 2013/0281883 A1* | 10/2013 | Nishida | A61B 5/7282 600/586 |
| 2013/0310657 A1 | 11/2013 | Sullivan et al. | |
| 2014/0188006 A1 | 7/2014 | Alshaer et al. | |

OTHER PUBLICATIONS

Cheng et. al., "Development of a Portable Device for Telemonitoring of Snoring and Obstructive Sleep Apnea Syndrome Symptoms," *Telemed. J. E. Health.* 14(1):55-68, 2008.

Dafna et. al., "Automatic Detection of Whole Night Snoring Events Using Non-Contact Microphone," *PLOS One* 8(12):e84139, 2013. (14 Pages).

Ng et. al., "Snore Signal Enhancement and Activity Detection via Translation-Invariant Wavelet Transform," *IEEE Tran. Biomed. Eng.* 55(10):2332-2342, 2008.

Roebuck et al., "A review of signals used in sleep analysis," *Physiol. Meas.* 35(1):R1-57, 2014. (73 Pages).

Rosenwein et al., "Breath-By-Breath Detection of Apneic Events for OSA Severity Estimation Using Non-Contact Audio Recordings," *37th Annual International Conference of the IEEE Engineering in Medicine and Biology Society*, Milan, Italy, Aug. 25-29, 2015, pp. 7688-7691.

Rosenwein et al., "Detection of Breathing Sounds During Sleep Using Non-Contact Audio Recordings," *36th Annual International Conference of the IEEE Engineering in Medicine and Biology Society*, Chicago, Illinois, USA, Aug. 26-30, 2014, pp. 1489-1492.

Snider et al., "Automatic Classification of Breathing Sounds During Sleep," *IEEE International Conference on Acoustics, Speech and Signal Processing (ICASSP)*, Vancouver, Canada, May 26-31, 2013, pp. 699-703.

* cited by examiner

| Events | PSG Results | | Detected Results | |
|---|---|---|---|---|
| | Start | Duration(s) | Start | Duration (s) |
| 1st Mixed Apnea | 1:38:59 | 27.1 | 1:38:54 | 28.7 |
| 2nd Mixed Apnea | 1:45:35 | 32.7 | 1:45:40 | 32.6 |
| 1st Obstructive Apnea | 1:39:32 | 26.1 | 1:39:33 | 28 |
| 2nd Obstructive Apnea | 1:40:04 | 25 | 1:40:08 | 21 |
| 1st Hypopnea | 2:06:18 | 12 | 2:06:20 | 13.6 |
| 2nd Hypopnea | 3:10:32 | 9 | 3:10:32 | 19.2 |
| 1st Central Apnea | 5:34:56 | 17.6 | 5:35:01 | 13.7 |

METHODS FOR DETECTING A SLEEP DISORDER AND SLEEP DISORDER DETECTION DEVICES

CROSS-REFERENCE TO RELATED APPLICATIONS

This application claims the benefit of Singapore Patent Application number 102016008478 filed 3 Feb. 2016, the entire contents of which are incorporated herein by reference for all purposes.

TECHNICAL FIELD

Various embodiments relate to methods for detecting a sleep disorder and sleep disorder detection devices.

BACKGROUND

Sleep disorders are common problems amongst the general population, regardless of gender and age. One of the serious sleep disorders is sleep apnea, which can result in significant medical complications such as hypertension, cognitive impairment, diabetes, as well as poor growth in children. Early diagnosis and prompt treatment are important to avoid these medical complications and to reduce morbidity. The gold standard for the diagnosis and assessment of sleep disorders is the overnight full polysomnography (PSG). However, PSG is not commonly available at clinics and is also expensive to administer because an extensive suite of medical equipment is required to conduct PSG. Therefore, it is difficult for the general public to obtain regular and inexpensive assessments of sleep disorders.

SUMMARY

According to various embodiments, there may be provided a method for detecting a sleep disorder, the method including: processing an audio signal, the audio signal including breathing sounds made by a subject when the subject is asleep; identifying intervals of the audio signal where breathing sounds are absent; and detecting the sleep disorder based on the identified intervals.

According to various embodiments, there may be provided a sleep disorder detection device including: a signal processing module configured to process an audio signal including breathing sounds made by a subject when the subject is asleep; an identification module configured to identify intervals of the audio signal where breathing sounds are absent; and a detection module configured to detect the sleep disorder based on the identified intervals.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the invention. In the following description, various embodiments are described with reference to the following drawings, in which.

DESCRIPTION

Figure 1:
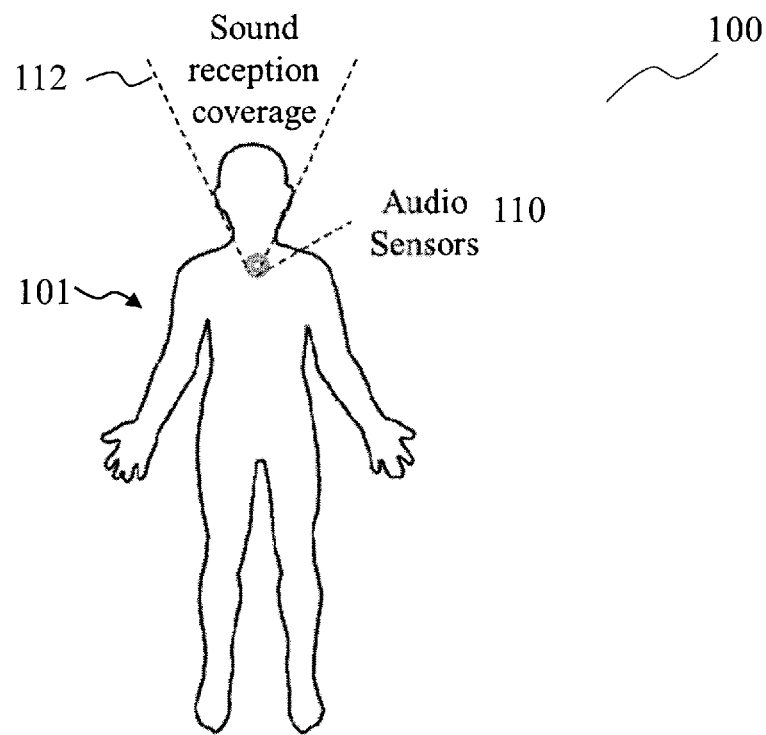
FIG. 1 shows a schematic diagram of a clinical set up to perform a method for detecting a sleep disorder according to various embodiments

Embodiments described below in context of the sleep disorder devices are analogously valid for the respective methods for detecting a sleep disorder, and vice versa. Furthermore, it will be understood that the embodiments described below may be combined, for example, a part of one embodiment may be combined with a part of another embodiment.

It will be understood that any property described herein for a specific device may also hold for any device described herein. It will be understood that any property described herein for a specific method may also hold for any method described herein. Furthermore, it will be understood that for any device or method described herein, not necessarily all the components or steps described must be enclosed in the device or method, but only some (but not all) components or steps may be enclosed.

In this context, the sleep disorder detection device as described in this description may include a memory which is for example used in the processing carried out in the device. A memory used in the embodiments may be a volatile memory, for example a DRAM (Dynamic Random Access Memory) or a non-volatile memory, for example a PROM (Programmable Read Only Memory), an EPROM (Erasable PROM), EEPROM (Electrically Erasable PROM), or a flash memory, e.g., a floating gate memory, a charge trapping memory, an MRAM (Magnetoresistive Random Access Memory) or a PCRAM (Phase Change Random Access Memory).

In an embodiment, a "module", a "sub-module" or a "circuit" may be understood as any kind of a logic implementing entity, which may be special purpose circuitry or a processor executing software stored in a memory, firmware, or any combination thereof. Thus, in an embodiment, a "module", a "sub-module" or a "circuit" may be a hardwired logic circuit or a programmable logic circuit such as a programmable processor, e.g. a microprocessor (e.g. a Complex Instruction Set Computer (CISC) processor or a Reduced Instruction Set Computer (RISC) processor). A "module", a "sub-module" or a "circuit" may also be a processor executing software, e.g. any kind of computer program, e.g. a computer program using a virtual machine code such as e.g. Java. Any other kind of implementation of the respective functions which will be described in more detail below may also be understood as a "module", a "sub-module" or a "circuit" in accordance with an alternative embodiment.

In the specification the term "comprising" shall be understood to have a broad meaning similar to the term "including" and will be understood to imply the inclusion of a stated integer or step or group of integers or steps but not the exclusion of any other integer or step or group of integers or steps. This definition also applies to variations on the term "comprising" such as "comprise" and "comprises".

The term "coupled" (or "connected") herein may be understood as electrically coupled or as mechanically coupled, for example attached or fixed, or just in contact without any fixation, and it will be understood that both direct coupling or indirect coupling (in other words: coupling without direct contact) may be provided.

In order that the invention may be readily understood and put into practical effect, various embodiments will now be described by way of examples and not limitations, and with reference to the figures.

In the context of various embodiments, the phrase "audio sensor" may be but is not limited to being interchangeably referred to as "acoustic sensor". The audio sensor may be a transducer configured to convert sound waves into an electrical signal that carries information about the sound waves.

In the context of various embodiments, the phrase "audio signal" may be but is not limited to being interchangeably referred to as "sound signal". The audio signal may be an electrical signal that carries information about sound waves.

In the context of various embodiments, the word "subject" may refer to a human being. The phrase "test subject" may refer to a human being who is being tested, in particular, for a sleep disorder.

In the context of various embodiments, the phrase "breathing sound" may be but is not limited to being interchangeably referred to as "respiratory sound".

According to various embodiments, a method for detecting a sleep disorder may be provided. The method may include analyzing breathing sounds of a subject when the subject is asleep, to find irregular or abnormal breathing patterns. The analysis may include identifying intervals where breathing sounds are absent. In other words, the method may include identifying time periods during the subject's sleep, where the subject does not breathe. The method may be able to detect sleep disorders such as obstructive sleep apnea syndrome, hypopnea or central sleep apnea.

FIG. 1 shows a schematic diagram 100 of a clinical set up to perform a method for detecting a sleep disorder according to various embodiments. The method may include placing at least one audio sensor 110 within proximity of the subject 101 to pick up respiratory sounds made by the subject 101 when the subject 101 is asleep. The audio sensor 110 may be able to receive sounds from a sound reception coverage area 112. As an example, the schematic diagram 100 shows that the audio sensor 110 is placed on the chest of the subject 101, close to the subject's upper airway such that the sound reception coverage area 112 may be a cone encompassing the subject's head. At this position, the audio sensor 110 may be able to receive respiratory sounds from the subject's upper airway, mouth and nose effectively. The respiratory sounds of the subject 101 may be monitored over a long duration, for example, throughout an entire night. To monitor the subject 101 without disturbing the subject's sleep, the equipment for monitoring the subject's sleep, referred herein as the sleep detection device, may be a portable wearable device, so that the subject 101 may wear the sleep detection device to sleep comfortably. For example, the sleep detection device may be housed in a belt or may be embedded in a textile material of a piece of clothing such as a shirt. The sleep disorder detection device may run on batteries instead of an external power supply so as to do away with power cables that may limit the subject's movements.

Alternatively, the sleep detection device may be a non-contact device that may monitor the subject 101 without directly contacting the subject 101. For example, the sleep disorder detection device may be packaged into a compact housing that may be brought along to any location, to be placed near where the subject 101 sleeps. For example, the compact housing may be placed inside a pillow or a mattress, or placed on furniture near to the bed, or hung on a wall or the ceiling. As compared to the multi-parametric PSG test which requires data on many body functions of a subject 101, the method described herein may detect the sleep disorders using only the respiratory sounds made by the subject 101 when the subject 101 is asleep. Therefore, unlike the PSG test which may require attaching sensors on various body parts of the subject 101, for example, attaching a flow thermometer to the subject's nostrils or mouth, attaching electrocardiogram electrodes on the subject's skin, or clipping the subject's fingers; the method only requires the use of audio sensors 110 that may collect the respiratory sounds without imposing discomfort on the subject 101. Also, the computational complexity of the method may be lower than the computational complexity of the PSG test. For example, the PSG test may require a minimum of twelve channels of data, including three channels for EEG, one channel for airflow, one channel for muscle movement from the chin, one channel for leg movements, two channels for eye movements, one channel for ECG, one channel for SpO2 and two channels for chest wall movement and abdominal wall movement. Often the PSG test may use more than thirty channels, including channels for respiratory sounds and sleep video. Therefore, the analysis of the PSG data may take as long as one to two weeks as the data in each channel has to be processed separately. In comparison, the method described herein may detect the sleep disorders by analyzing the respiratory sounds alone, without having to analyze the vast amount of data required in a typical PSG test. Also, the PSG test analyses the snore signals in the audio signal one snore signal at a time, whereas the method may be able to process the silent intervals of the audio signal simultaneously. The method also analyses portions of the audio signal that occur just before and after the silent intervals, to provide high accuracy in the detection of the sleep disorder.

The method may include placing more audio sensors 110 around the subject 101. At least one audio sensor 110 may be positioned near the subject's upper airway to primarily receive the subject's respiratory sounds. At least one other audio sensor 110 may be positioned at other locations near to the subject 101, but away from the subject's upper airway, so as to primarily receive the ambient noise (in other words: background noise) and interfering sounds. The interfering sounds may include conversations in the background, or unwanted sounds generated by the subject 101. The method may include using signal conditioning circuits to remove the ambient noise and to increase the amplitude of the breathing sounds, in the audio signals received by the audio sensors 110. The signal conditioning circuits may also combine the audio signals received by the audio sensors 110 positioned at various locations. The signal conditioning circuits may include signal processing algorithms for performing adaptive noise cancellation.

Figure 2:
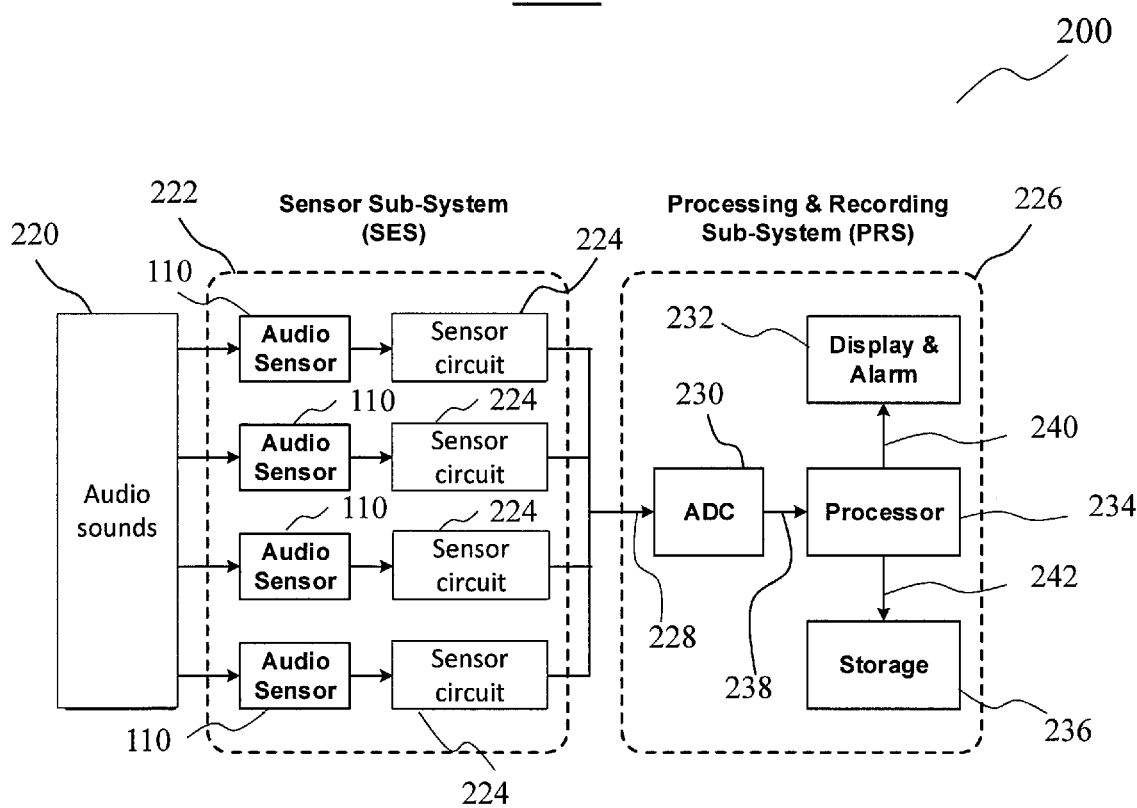
FIG. 2 shows a functional block diagram of a sleep disorder detection device according to various embodiments.

FIG. 2 shows a functional block diagram of a sleep disorder detection device 200 according to various embodiments. The sleep disorder detection device 200 may include a sensor sub-system (SES) 222 and a processing and recording sub-system (PRS) 226. The SES 222 may be configured to receive audio sounds 220 and may be further configured to provide an audio signal 228 to the PRS 226. The SES 222 may include at least one audio sensor 110. The audio sensor 110 may be configured to receive the audio sounds 220 and may be further configured to provide an audio output based on the audio sounds 220. The SES 222 may further include at least one sensor circuit 224 configured to process the audio output of the audio sensor 110 to provide a sensor output. The audio signal 228 may be one of the audio output or the sensor output. The audio signal 228 may carry information on the audio sounds 220. The PRS 226 may be configured to receive the audio signal 228 and may be further configured to process the audio signal 228 to determine if the audio signal 228 is indicative of a sleep disorder. The PRS 226 may also be configured to record the audio signal 228, as well as any intermediate processing data and the end results of the processing.

The SES 222 may be a sound receiving system such as a microphone or a stethoscope. The audio sensor 110 in the SES 222 may be a transducer configured to convert sound waves into an electrical signal. The electrical signal may be the audio output. The sensor circuit 224 may be configured to receive the electrical signal, i.e. the audio output. The sensor circuit 224 may also be referred herein as a signal conditioning circuit. The sensor circuit 224 may include at least one of a filter or an amplifier. The filter may be configured to remove certain components of the electrical signal according to a predetermined filtering function. The amplifier may be configured to increase the amplitude of the electrical signal according to a predetermined amplification function. The filter and the amplifier may work in conjunction to boost the amplitude of certain components of the electrical signal while suppressing other components of the electrical signal. For example, the filter and the amplifier may suppress out-of-band noise and interferences, while amplifying the power of target signals. In other words, the sensor circuit 224 may increase the signal-to-noise ratio of the electrical signal. The sensor circuit 224 may be configured to process electrical signals in a frequency range from about 0 Hz to about 44,125,000 Hz, for example, from about 60 Hz to about 4000 Hz. The filtering function of the filter may include a stop band having an attenuation that ranges from about 10 dB to about 80 dB, for example from about 10 dB to about 50 dB, for example about 30 dB. The SES 222 may include a plurality of sensor circuits 224 wherein each sensor circuit 224 may be configured to receive the electrical signal from a respective audio sensor 110. Alternatively, each sensor circuit 224 may be configured to receive electrical signals from a plurality of audio sensors 110. Each sensor circuit 224 may be configured to generate an audio signal 228 based on the received electrical signal(s) and the predetermined criteria.

The PRS 226 may include an analog-to-digital converter (ADC) 230 and a processor 234. The PRS 226 may further include a display and alarm sub-system 232, and may further include a storage sub-system 236. The ADC 230 may be a multi-channel ADC that is configured to simultaneously convert the plurality of audio signals 228 into a corresponding plurality of digital audio signals 238. The ADC 230 may also be a single-channel ADC that is configured to digitize the plurality of audio signals 228, one at a time, into a corresponding plurality of digital audio signals 238. Alternatively, the plurality of audio signals 228 may be combined into a combined audio signal 228 by a signal combiner within the SES 222 such that the ADC 230 may receive the combined audio signal 228. The ADC 230 may then digitize the combined audio signal 228 into a single digital audio signal 238. The ADC 230 may be configured to sample analog signals at a sampling rate in a range of about 1000 to about 44,125,000 samples per second, for example, in a range of about 1000 to about 20,000 samples per second, for example about 8,000 samples per second. The ADC 230 may be configured to sample at a resolution that is in a range of about 8 to about 64 bits, for example about 16 bits. The processor 234 may be configured to suppress background noise or interfering sounds from the digital signal 238 and may be further configured to detect the presence of sleep disorders. The processor 234 may generate a first processor output 240 that may contain information on the detection results. The processor 234 may provide the first processor output 240 to the display and alarm sub-system 232. The display and alarm sub-system 232 may be configured to display the detection results. The display and alarm sub-system 232 may include a display such as a light emitting diode screen, for displaying the detection results. The processor 234 may also provide the first processor output 240 to an external device, for example a smart phone or a computer, for displaying the detection results. The processor 234 may also provide a second processor output 242 to the storage sub-system 236. The second processor output 242 may include the same information as the first processor output 240, and may further include the digital audio signals 238 or other intermediate data generated in the PRS 226. The second processor output 242 may be stored in the storage sub-system 236 for subsequent analysis. The processor 234 may be communicatively coupled to each of the display and alarm sub-system 232 and the storage sub-system 236 via one of a wired connection or a wireless connection. The wireless connection may be one of a WiFi connection, a Bluetooth connection, or an infrared connection. The PRS 226 may further include a transmitter and a receiver. The transmitter may be configured to transmit at least one of the first processor output 240 from the processor 234 to the display and alarm sub-system 232, or the second processor output 242 from the processor 234 to the storage sub-system 236, via the wireless connection. The receiver may be configured to receive data or commands from any one of the display and alarm sub-system 232 or the storage sub-system 236 to the processor 234, via the wireless connection. For example, the data may include intermediate signals that the processor 234 may request from the storage sub-system 236. The commands may include requests or instructions from the display and alarm sub-system 232, for example requests for the first processor output 240 to be sent.

Figure 3:
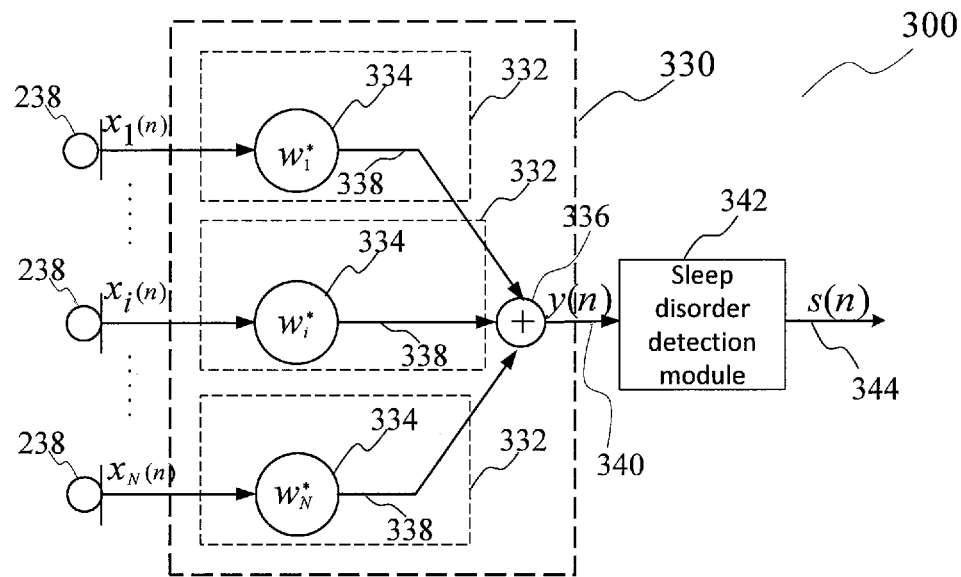
FIG. 3 shows a block diagram of the processor of FIG. 2.

FIG. 3 shows a block diagram 300 of the processor 234. The processor 234 may include a signal combining module 330 and a sleep disorder detection module 342. The signal combining module 330 may be the signal combiner in the PRS 226. The signal combining module 330 and the sleep disorder detection module 342 may be implemented either in software or in hardware. The signal combining module 330 may be configured to combine a plurality of digital signals into a single output stream. The signal combining module 330 may receive the plurality of digital audio signals 238 from the ADC 230. The signal combining module 330 may include a bank of filters 332. Each filter 332 may be configured to multiply a respective digital audio signal 238 by a respective weight $w_i$ 334, to generate a respective weighted signal 338. The weights 334 may be complex values. The signal combining module 330 may further include an adder 336. The adder 336 may be configured to sum the plurality of weighted signals 338 to provide a single output stream, also referred herein as the combined signal 340. The combined signal 340 may be a single channel signal which may be processed in the same way as the digital audio signal derived from a single audio sensor 110. The sleep disorder detection module 342 may be configured to receive the combined signal 340. The sleep disorder detection module 342 may include circuits or algorithms to generate detection results 344. The generated detection results 344 may be part of the first processor output 240 or the second processor output 242.

According to various embodiments, the SES 222 may include an array of audio sensors 110. The audio sensors 110 of the array may be spaced apart from one another, such that each audio sensor 110 may generate a respective positional audio signal. The positional audio signal may contain information of the sound received at the position of the audio sensor 110. The signal combining module 330 may be used to combine the positional audio signals into the combined signal 340. Each digital audio signal 238 may be derived from the respective positional audio signal. The array of audio sensors 110 may enhance the signal-to-noise ratio (SNR) of the signal of interest which are the respiratory sounds, and may also suppress interfering signals received by the audio sensors 110. The signal combining module 330 may employ any one of beam forming technique, null steering technique, signal correlation-based technique, or any other technique that is capable of exploiting correlative information captured in the various audio sensors 110. For example, the array of audio sensors 110 may be configured to generate the largest amplification in the direction of the signal of interest, in other words, towards the upper airway, mouth and/or nose of the subject 101, while suppressing audio signals arriving from other directions. As a result, the signal quality of respiratory sounds may be improved over an audio signal from a single audio sensor 110. The sleep disorder detection device 200 may be operated at a distance from the subject 101, for example, on a bedside table instead of being attached to the subject 101, by virtue of the signal combining process of the signal combining module 330.

According to various embodiments, the ADC 230 may be implemented in the SES 222 instead of implemented in the PRS 226. The signal combining module 330 may also be implemented in the SES 222 instead of implemented in the processor 234.

Figure 4:
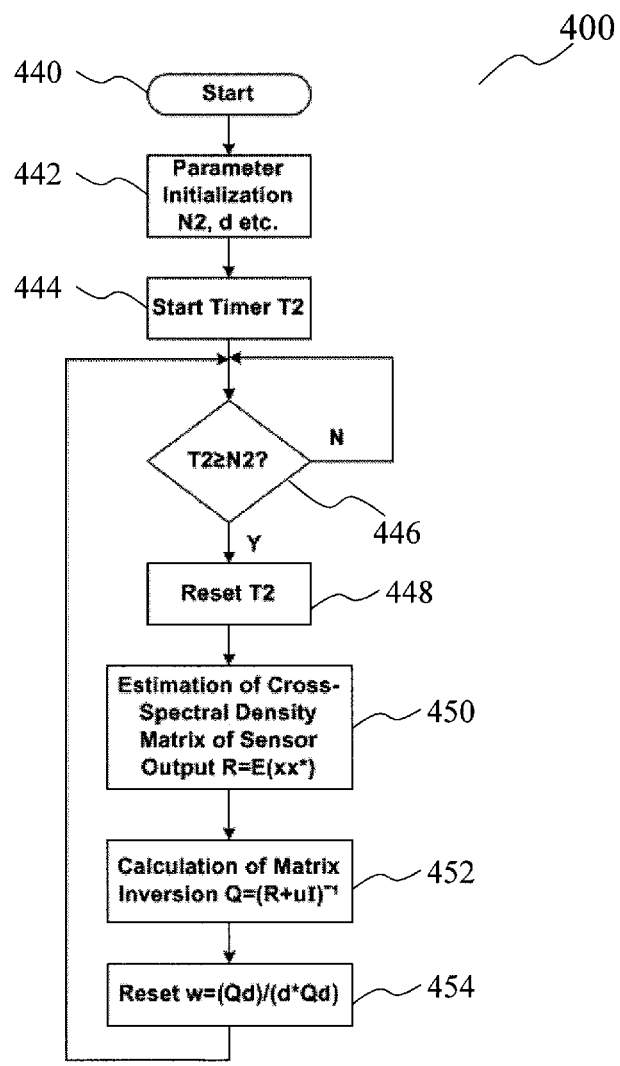
FIG. 4 shows a flow chart of an operation for computing the weights in the signal combining module.

FIG. 4 shows a flow chart 400 of an operation for computing the weights 334. The signal combining module 330 may be configured to compute the weights 334. The operation may include computing the weights 334 based on beamforming technique. From a start state 440, the operation may proceed to 442, where the parameters are initialized. At 442, parameters are initialized. The parameters include d, $w_0$, $N_2$ and $T_2$, where d denotes the steering vector of the array of audio sensors, $w_0$ represents the initial value of the weight w of the filter, $\mu$ is the Lagrange multiplier whose value is ranged from 0 to 1, N2 represents a time duration (for e.g. about 4 seconds) and $T_2$ denotes a timer. At 444, the timer may be started. At 446, it may be evaluated as to whether T2 is equal to or more than N2. If T2 is more than or equal to N2, the operation may proceed to 448. If T2 is less than N2, the operation may return to 446. At 448, T2 may be reset. At 450, the cross-spectral density matrix of the sensor output may be estimated. The cross-spectral density matrix R may be computed as R=E(xx*), where x denotes a vector of audio sensor outputs (in other words: digital audio signal 238) and "*" represents conjugate transpose. At 452, the matrix inversion may be calculated as $Q=(R+uI)^{-1}$, where u is a factor ranged 0 to 1 (for example: 0.001) and I denotes a unity matrix. At 454, the weights 334 may be computed as w=(Qd)/(d*Qd), where w denotes a vector of weights 334. Following 454, the operation may return to 446. In other words, for every time duration N2, the cross-spectral density matrix R and its inversion may be estimated, and the weights of the filter may be updated.

Figure 5:
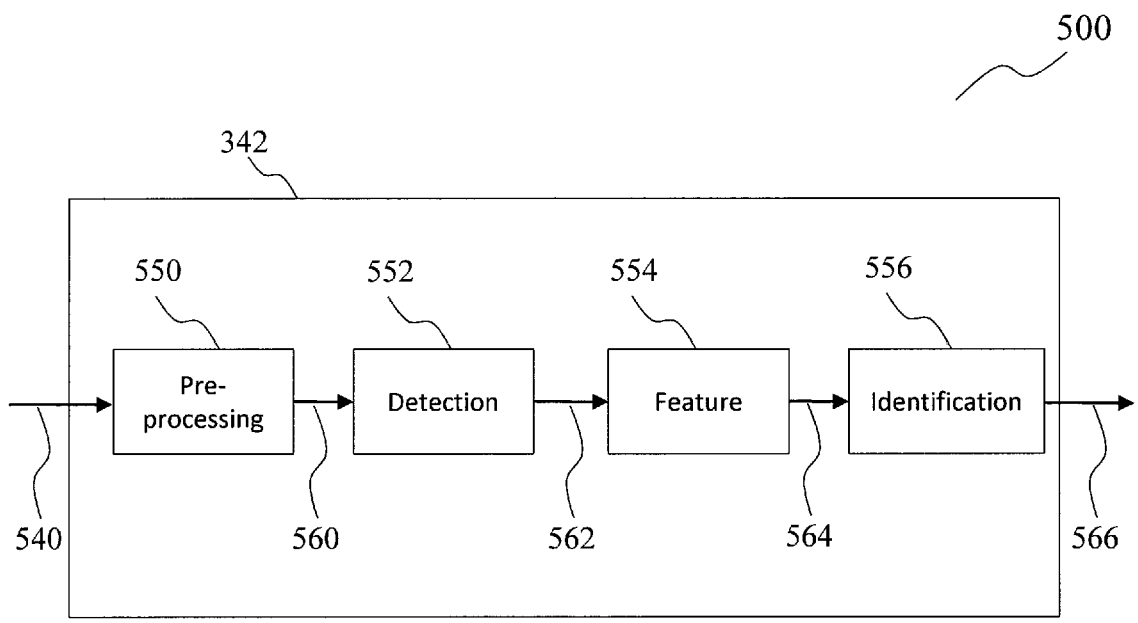
FIG. 5 shows a block diagram of the sleep disorder detection module.

FIG. 5 shows a block diagram 500 of the sleep disorder detection module 342. The sleep disorder detection module 342 may receive an input signal 540 and may generate an output signal 566. The input signal 540 may be the combined signal 340 received from the signal combining module 330. The output signal 566 may be the detection results 344. The sleep disorder detection module 342 may include a pre-processing module 550, a detection module 552, a feature module 554 and an identification module 556.

Figure 6:
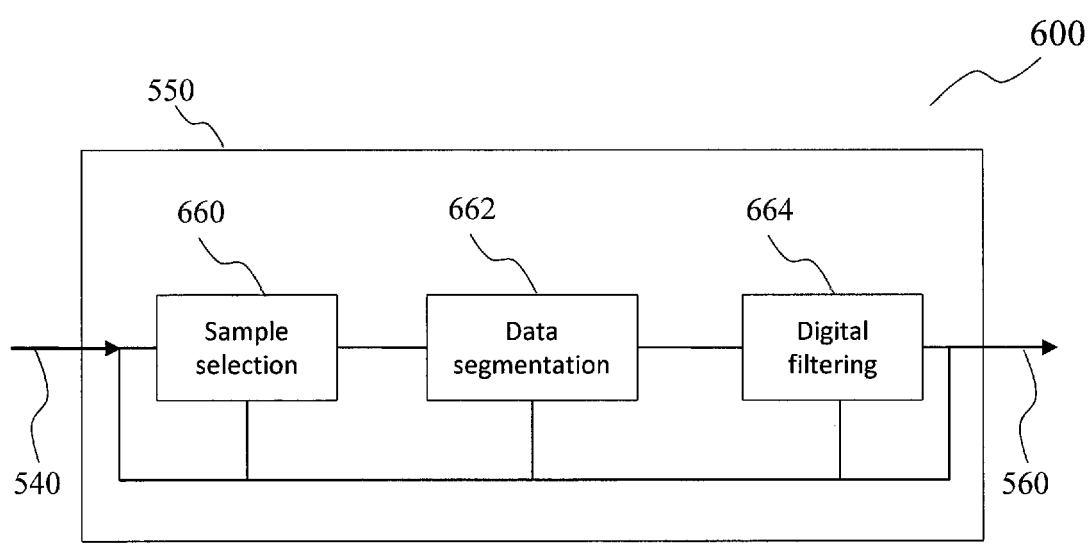
FIG. 6 shows a block diagram of the pre-processing module.

FIG. 6 shows a block diagram 600 of the pre-processing module 550. The pre-processing module 550 may provide a pre-processed signal 560 to the detection module 552, based on the input signal 540. The pre-processing module 550 may include a sample selection sub-module 660, a data segmentation sub-module 662 and a digital filtering sub-module 664. The sample selection sub-module 660 may be configured to choose a suitable set of data to be processed according to the requirements and conditions of the application. The sample selection sub-module 660 may receive the input signal 540 and may first store the input signal 540 temporarily in a buffer. The sample selection sub-module 660 may select samples from the input signal 540 upon receiving a data selection indicator from a controller. The process of sample selection may be used to exclude extraordinary samples from the input signal 540 or to down-sample the input signal 540. The data segmentation sub-module 662 may be configured to group the data into segments, so that the data segments may be processed even as further data is still being received by the sleep disorder detection device 200. For example, the entire process of receiving the respiratory sounds of the subject may be as long as the sleep duration of the subject, which may be about eight to twelve hours. By grouping the data into segments, a first data segment may be processed in the pre-processing module 550 and subsequent modules in the sleep disorder device 200, even while respiratory sounds are still being collected. The data segmentation sub-module 662 may group data into segments that contain sufficient information for analysis by the subsequent modules of the sleep disorder device 200. The data segmentation sub-module 662 may provide data segments that each include at least one full breathing cycle or a duration longer than that of an apnea. The digital filtering sub-module 664 may be configured to filter the data to reduce noise and interference or to remove components that are of no interest to the detection of the sleep disorder. For example the digital filtering sub-module 664 may suppress frequency components that are outside of the bandwidth of interest. The digital filtering sub-module 664 may also remove artefacts from the input signal 540. The digital filtering sub-module 664 may be further configured to normalize the power levels of the input signal 540, so that the audio signals received from different subjects may be adjusted to at least substantially similar power levels. For example, a first subject may breathe louder than a second subject. The digital filtering sub-module 664 may adjust the power levels of the audio signal such that the average power level at least substantially matches a preset benchmark. Digital filtering may also be applied to reduce noise and interference. The order of these processing steps may be in any combination depending on the techniques to be used in the practice.

Figure 7:
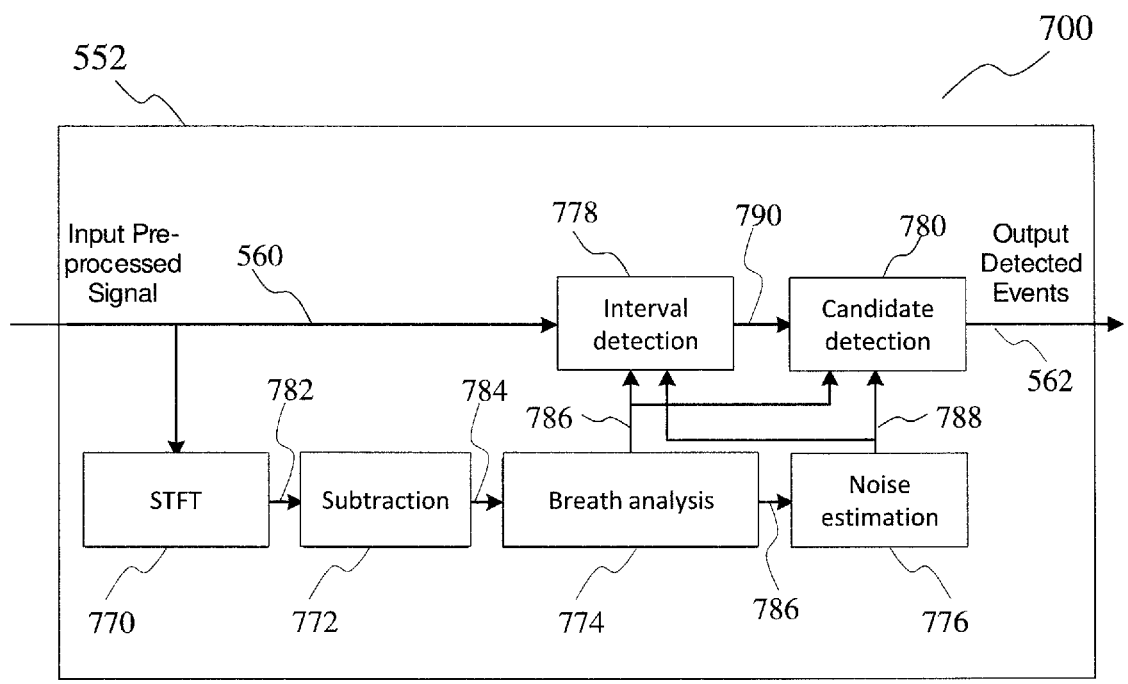
FIG. 7 shows a block diagram of the detection module.

FIG. 7 shows a block diagram 700 of the detection module 552. The detection module 552 may receive the pre-processed signal 560 from the pre-processing module 550 and may process the pre-processed signal 560 in both the time domain and the frequency domain to provide a detection signal 562 to the feature module 554. The detection signal 562 may be indicative of portions of the audio signal that have a high likelihood of corresponding to abnormal breathing events, also referred herein as candidate events. The event detection module 552 may include a short time Fourier Transform (STFT) sub-module 770, a subtraction sub-module 772, a breath analysis sub-module 774, a noise estimation sub-module 776, a candidate detection sub-module 780 and an interval detection sub-module 778. The STFT sub-module 770 may generate a STFT output 782 based on the pre-processed signal 560. The subtraction sub-module 772 may generate a dominant component output 784 based on the STFT output 782. The breath analysis sub-module 774 may generate a breath analysis output 786 based on the dominant component output 784, by analyzing the entropy values of the dominant component output 784. The noise estimation sub-module 776 may generate a noise estimation output 788 based on the breath analysis output 786. The interval detection sub-module 778 may generate an interval detection output 790 based on at least one of the pre-processed signal 560 or the breath analysis output 786. The candidate detection sub-module 780 may generate the detection signal 562 based on at least one of the interval detection output 790, the noise estimation output 788 or the breath analysis output 786.

Figure 8:
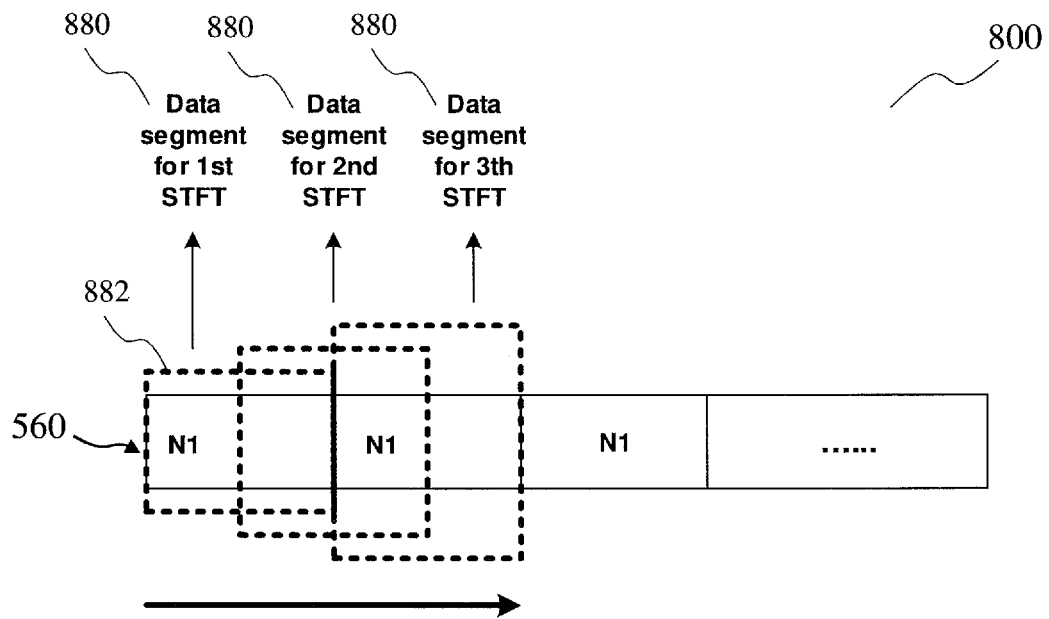
FIG. 8 shows a diagram illustrating the process of STFT.

FIG. 8 shows a diagram 800 illustrating the process of STFT. The STFT sub-module 770 may be configured to perform STFT on the pre-processed signal 560. The STFT sub-module 770 may segment the pre-processed signal 560 in the time domain, into a plurality of data segments 880. Each data segment 880 may overlap with its immediate neighboring data segments 880. The overlap between the neighboring data segments 880 may range from 0% to 100%. The diagram 800 shows an example where the overlap between neighboring data segments 880 is about 50%. Each data segment 880 may be equal in time duration. The time duration of each data segment 880 may be represented by the width of the sliding window 882. The width of the sliding window 882 may be denoted as $N_1$. Each data segment 880 may include $R_s * N_1 = N_m$ data samples, where $R_s$ is the sampling rate of the ADC 230. The STFT sub-module 770 may apply Fast Fourier Transform (FFT) to each data segment 880 at multiples of a predetermined time period $T_1$. In other words, the STFT sub-module 770 may apply FFT to each data segment 880 at a frequency equal to the inverse of $T_1$. $T_1$ may be set to a suitable value, for example, $T_1 = 0.5 * N_1$. In various embodiments, $N_1$ may range from 10 s to 1000 ms. In various embodiments, $N_1$ may be 64 ms. The STFT sub-module 770 may transform the data samples collected within $T_1$ from each data segment 880 into the frequency domain, in other words, to obtain a respective Fourier spectrum for each data segment 880. The Fourier spectra of the plurality of data segments 880 may be combined to obtain the SFTF output 782.

The subtraction sub-module 772 may be configured to subtract a baseline power level from the power spectrum of the SFTF output 782. The subtraction sub-module 772 may determine the baseline power level L (n) of the power spectrum X (n) of the SFTF output 782, by average filtering X(n) according to Equation (1):

$$L(n) = \frac{1}{M} \sum_{m=-M/2}^{M/2} X(n+m), \quad [1]$$

where $$X(n) = \begin{cases} \|S(n)\|^2 & n = 1, 2, \ldots N_{\mathit{fft}}/2 \\ 0 & \text{otherwise} \end{cases}, \quad [2]$$

where S(n) denotes the SFTF output 782 and M denotes the length of the averaging filter. M may range from 0 to $N_{\mathit{fft}}$, for example M may be equal to $N_{\mathit{fft}}/4$. The subtraction sub-module 772 may compare the power level of each frequency component of the STFT output 782 to the baseline power level. The subtraction sub-module 772 may remove non-dominant frequency components according to Equation (3).

$$c(n) = \begin{cases} X(n) - L(n) & \text{if } X(n) > L(n) \\ 0 & \text{if } X(n) \le L(n) \end{cases} \quad [3]$$

where n=1,2, . . . , $N_{\mathit{fft}}/2$ and c(n) denotes the dominant component output 784. In other words, frequency components with a power level that is less than or equal to the baseline power level, also referred herein as non-dominant frequency components, may be removed from the SFTF output 782. Therefore, the dominant component output 784 may include the dominant frequency components of the SFTF output 782 but may exclude the non-dominant frequency components of the SFTF output 782. With the non-dominant frequency components removed, the computational complexity for the subsequent processes may be reduced, thereby saving on processing time and power. Alternatively, the subtraction sub-module 772 may replace the non-dominant frequency components with a small value instead of zero to provide an enhanced dominant component output to the breath analysis sub-module 774.

The breath analysis sub-module 774 may calculate the entropy values of the frequency components of the dominant component output 784, in other words, the entropy values of the dominant frequency components. The entropy of each frequency component may be a measure of the expected value of the information contained in the frequency component. The breath analysis sub-module 774 may compute a weight, $P_n$, for each frequency component may be measured by the ratio between the power level of the specific dominant frequency component and the sum of all these dominant frequency components. The weights $P_n$, may be computed using Equation (4):

$$P_n = C_n / \Sigma_{n=1}^{N} C_n, \quad n=1,2,\ldots,N, \quad [4]$$

where N denotes the quantity of dominant frequency components, n denotes an index of the frequency component, and the power levels (or amplitude or equivalent) of the respective frequency components are denoted by $C_1$, $C_2, \ldots, C_N$. The breath analysis sub-module 774 may then calculate the entropy of each dominant frequency component based on the weights $P_n$, using Equation (5):

$$E = -\Sigma_{n=1}^{N} P_n \log P_n. \quad [5]$$

After smoothing the entropy values of the dominant frequency components along the time axis, the breath analysis sub-module 774 may estimate the breathing cycle by applying the autocorrelation function to the entropy values that were smoothened along the time axis. The application of the autocorrelation function may reveal the quasi-periodic characteristics of the respiratory signal. A normal breathing cycle may include an inspiration (in other words: inhalation of air), an expiration (in other words: exhalation of air), and a short pause in between the inspiration and the expiration. The breath analysis sub-module 774 may identify the inspiratory phase, i.e. the duration of inspiration, and the expiratory phase, i.e. the duration of expiration, of the breathing cycle based on the entropy values. The inspiratory phase and the expiratory phase may have relatively small values of entropy as compared to the pauses between the inspiration and expiration. Therefore, each of the inspiratory phase, the expiratory phase and the pause of each breath cycle may be identified. The breath analysis output 786 may contain information on each of the inspiratory phases, the expiratory phases and the pauses.

The noise estimation sub-module 776 may be configured to estimate the background noise level based on the breath analysis output 786. The pauses in between the inspiratory phase and the expiratory phase may be assumed to be devoid of breathing sounds. Therefore, the noise estimation sub-module 776 may compute the statistical characteristics of the background noise based on the identified pauses of each breath cycle. The statistical characteristics may include parameters such as mean value and standard deviation of the power levels of the identified pauses. The noise estimation output 788 may include the computer statistical characteristics.

The interval detection sub-module 778 may identify intervals where breathing sounds are absent in the pre-processed signal 560, based on comparing the power levels in the pre-processed signal 560 against the computed power level of the background noise. The intervals where breathing sounds are absent may also be referred herein as silent intervals. Segments in the pre-processed signal 560 where the power level is lower than the power level of inspiration and expiration but at least substantially similar to the power level of background noise may be identified as being silent intervals. The interval detection sub-module 778 may calculate the power envelope of the pre-processed signal 560, and then compare the calculated power envelope to a threshold. The threshold may be defined as a function of the statistical characteristics computed by the noise estimation sub-module 776. As an example, the threshold may be defined as the mean value of the background noise plus three times the standard deviation value of the background noise. The interval detection sub-module 778 may identify portions of the pre-processed signal 560 with power level below the threshold as the silent intervals, and may identify all remaining portions of the pre-processed signal 560 as ventilation portions (in other words: parts of the audio signal where breathing sounds are present). The interval detection sub-module 778 may calculate and store the durations of each silent interval and each ventilation portion.

The candidate detection sub-module 780 may detect possible sleep disorder events, also referred herein as candidate events, by comparing the silent intervals identified by the interval detection sub-module 778 against a duration threshold associated with the sleep disorder. For example, apnea for an adult may be defined as a lack of breathing for at least 10 seconds in between breaths. The duration threshold for detecting apnea for an adult may be 10 seconds. The candidate detection sub-module 780 may identify a silent interval as a candidate event if the silent interval equals or exceeds the duration threshold. The duration threshold may be adapted to the application scenario at the initialization stage of operating the sleep disorder device 200. For example, the definition of apnea for children may be different from the definition of apnea for adults, and as such, the duration threshold may be adapted accordingly. In addition, the candidate detection sub-module 780 may also check the duration of the ventilation portions between two successive silent intervals. If the duration of the ventilation portion between two successive silent intervals is shorter than a percentage threshold of the average duration of the ventilation portions as calculated by the interval detection sub-module 778, the two successive silent intervals may be treated as candidate events even if the duration of each silent interval is shorter than the duration threshold. The percentage threshold may be, for example, defined as 25%.

Figure 9:
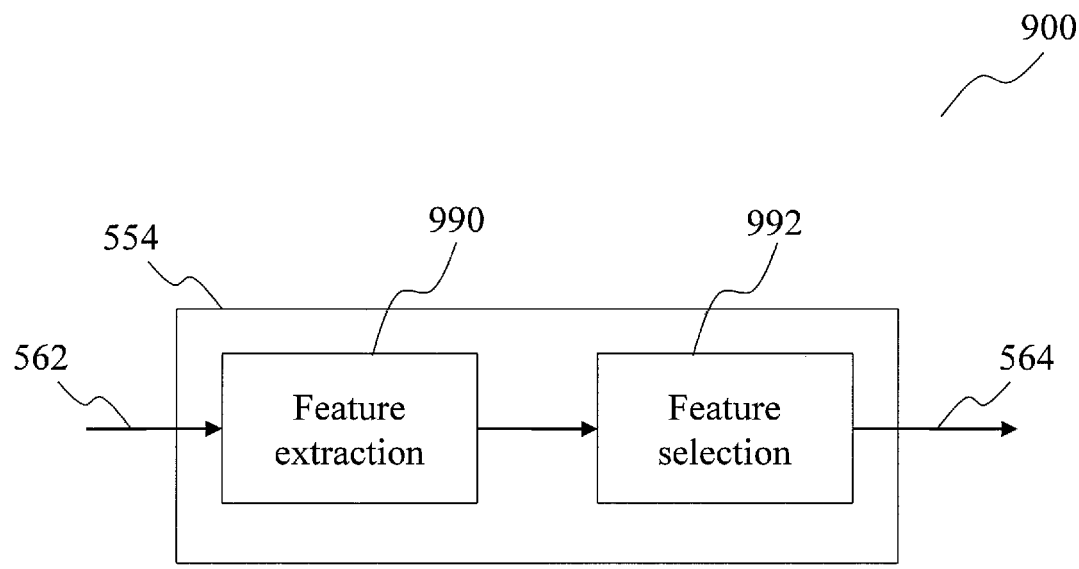
FIG. 9 shows a block diagram of the feature module.

FIG. 9 shows a block diagram 900 of the feature module 554. The feature module 554 may be configured to provide selected extracted features 564 to the identification module 556 based on the detection signal 562. The feature module 554 may include a feature extraction sub-module 990 and a feature selection sub-module 992. The feature extraction sub-module 990 may extract features from each candidate event. The feature extraction sub-module 990 may also extract features from the ventilation portions that occur immediately before and immediately after each candidate event, herein also referred to as candidate-associated ventilation portions. The feature extraction sub-module 990 may calculate a vector of features to represent the characteristics of each candidate event, and may also calculate a vector of features to represent the characteristics of each candidate-associated ventilation portions. The vector of features may include at least one of FFT coefficients, mel-frequency cepstral coefficients (MFCC), linear prediction coefficients, perceptual linear prediction coefficients or wavelet transform coefficients. In the experiment described in the following paragraphs, the vector of features included MFCC. The feature selection sub-module 992 may be configured to identify a subset of features from the vectors of features, that is the most useful in the classification stage. In other words, the feature selection sub-module 992 may be configured to identify the subset of features that may be the most relevant for the purpose of determining whether the candidate events are indicative of the sleep disorder. The most useful or the most relevant features may be features that occur prominently among the candidate events but hardly surface in non-candidate events. By identifying the relevant subset of features, the feature selection sub-module 992 may reduce the computational complexity required in the identification module 556. The feature selection sub-module 992 may identify the subset of features by applying a dimension reduction method. The dimension reduction method may be one of principal components analysis, independent component analysis, canonical correlation analysis or Fisher's linear discriminant (FLD). In the experiment described in the following paragraphs, the dimension reduction method used is the FLD method.

Figure 10:
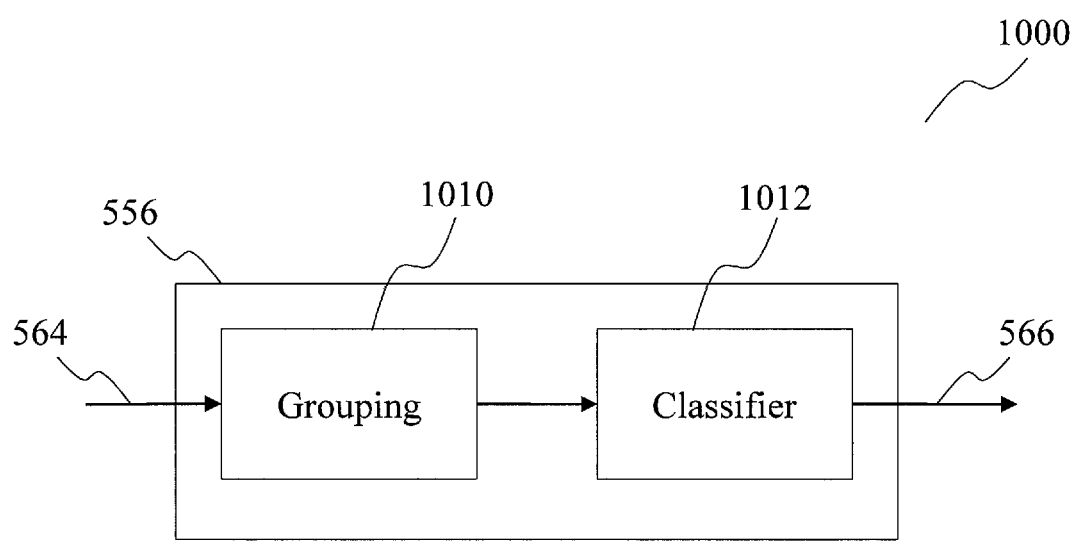
FIG. 10 shows a block diagram of the identification module.

FIG. 10 shows a block diagram 1000 of the identification module 556. The identification module 556 may detect the presence (or absence) of the sleep disorder based on the selected extracted features 564. The identification module 556 may include a grouping sub-module 1010 and a classifier sub-module 1012. The grouping sub-module 1010 may be configured to combine candidate events according to a set of empirical rules. For example, if two successive silent portions are separated by a non-silent part shorter than 25% of the average duration of the ventilation portions, the non-silent part may be identified as an effort of breath where no actual ventilation occurs. Therefore, the grouping sub-module 1010 may group the two successive silent portions as a silent portion. In other words, the duration of the newly formed silent portion may be the sum of the duration of the two successive silent portions. The grouping sub-module 1010 may also group the short non-silent part and the newly formed silent portion to provide a candidate event. The candidate event may be as long as several breathing cycles. The classifier sub-module 1012 may be a software engine driven by pre-defined algorithms. The classifier sub-module 1012 may be used to assort candidate events into different categories based on their features. The classifier sub-module 1012 may use any classification methods, for example Bayes networks, decision trees, k-means clustering, kth-nearest neighbour, multivariate discriminant analysis, support vector machines, neural networks or Extreme Learning Machine (ELM). In the experiment described in the following paragraphs, the classification method used is the ELM. The ELM is a learning algorithm which may randomly assign all the hidden nodes parameters of generalized Single-hidden Layer Feedforward Networks (SLFNs) and may analytically determine the output weights of ELM method. The features feeding to the classifier sub-module 1012 may be the duration of the silent intervals identified in the detection sub-module 552 and the selected extracted features 564 from the feature selection sub-module 992. The output signal 566 of the classifier sub-module 1012 may be the final results of the sleep disorder detection module 342. The output signal 566 may indicate whether the sleep disorder is detected.

The display and alarm sub-system 232 may receive the output signal 566 as part of the first processor output 240. The display and alarm sub-system 232 may display the detection results 344 contained in the output signal 566, and may generate an alarm signal if the output signal 566 indicates that detection of the sleep disorder. The storage sub-system 236 may also receive the output signal 566 as part of the second processor output 242. The storage sub-system 236 may store the output signal 566. The processor 234 may also transmit the output signal to external devices, for example a remote server in the hospital network. The storage sub-system 236 may also store the audio sounds 220 where the sleep disorder is detected, or may store the candidate events where the sleep disorder is detected.

According to various embodiments, the sleep disorder detection device may be adapted to detect other types of respiratory disorders, such as lung diseases. The interval detection sub-module 778 may be configured to detect a distinctive characteristic of the respiratory disorder. The respiratory disorder may cause a subject to produce abnormal breathing sounds, i.e. an adventitious sound, such as a wheezing sound or a coughing sound. The interval detection sub-module 778 may be adapted to detect the adventitious sound.

According to various embodiments, the sleep disorder detection device may be adapted to monitor environmental sounds for detecting dangerous events. The interval detection sub-module 778 may be configured to detect abnormal sounds relating to dangerous events, for example the sound of boiling water.

According to various embodiments, the sleep disorder detection device may be used as an audio recording device.

In the following, an experiment and the results of the experiment will be described. The experiment was conducted using respiratory sounds captured from patients in local hospitals, to validate the method for detecting a sleep disorder according to various embodiments. The experiment showed that the method was able to achieve an accuracy of 78.67% in detecting apnea and an accuracy of 82.93% in detecting hypopnea. The average detection accuracy of both apnea and hypopnea combined was 80.17%, and the average true negative rate was 82.89%.

Figure 11:
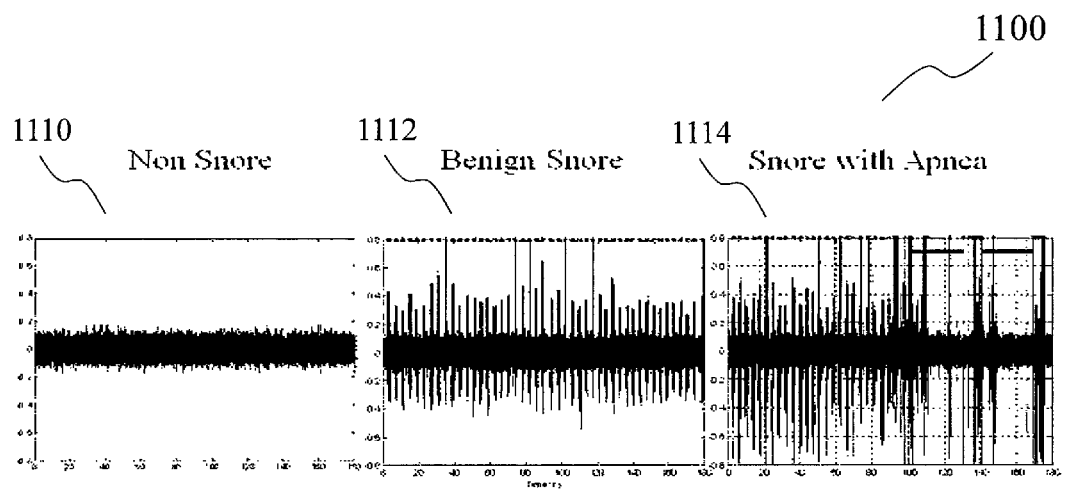
FIG. 11 shows a group of graphs showing oscillograms of audio signals of different respiratory patterns.

FIG. 11 shows a group of graphs 1100 showing oscillograms of audio signals of different respiratory patterns. The graphs 1100 may be examples of results displayed at the output signal 566 of the identification sub-module 556. The group of graphs 1100 includes a first oscillogram 1110, a second oscillogram 1112 and a third oscillogram 1114. Each of the first oscillogram 1110, the second oscillogram 1112 and the third oscillogram 1114 has a horizontal axis indicating time and a vertical axis indicating amplitude. The first oscillogram 1110 shows an example of an audio signal of regular breathing sounds, where the amplitude is fairly constant with respect to time. The second oscillogram 1112 shows an example of an audio signal of benign snoring sounds. In other words, the audio signal shows that the subject is snoring while maintaining regular breathing. The second oscillogram 1112 shows a periodic fluctuation in the amplitude but the time gap between each fluctuation is small. The third oscillogram 1114 shows an example of an audio signal of snoring with apnea. The third oscillogram 1114 shows that the time gap between the snores became fairly large in the second half of the audio signal, as compared to the time gap between the snores in the first half of the audio signal. The second half of the audio signal indicates occurrence of apnea.

Figure 12:
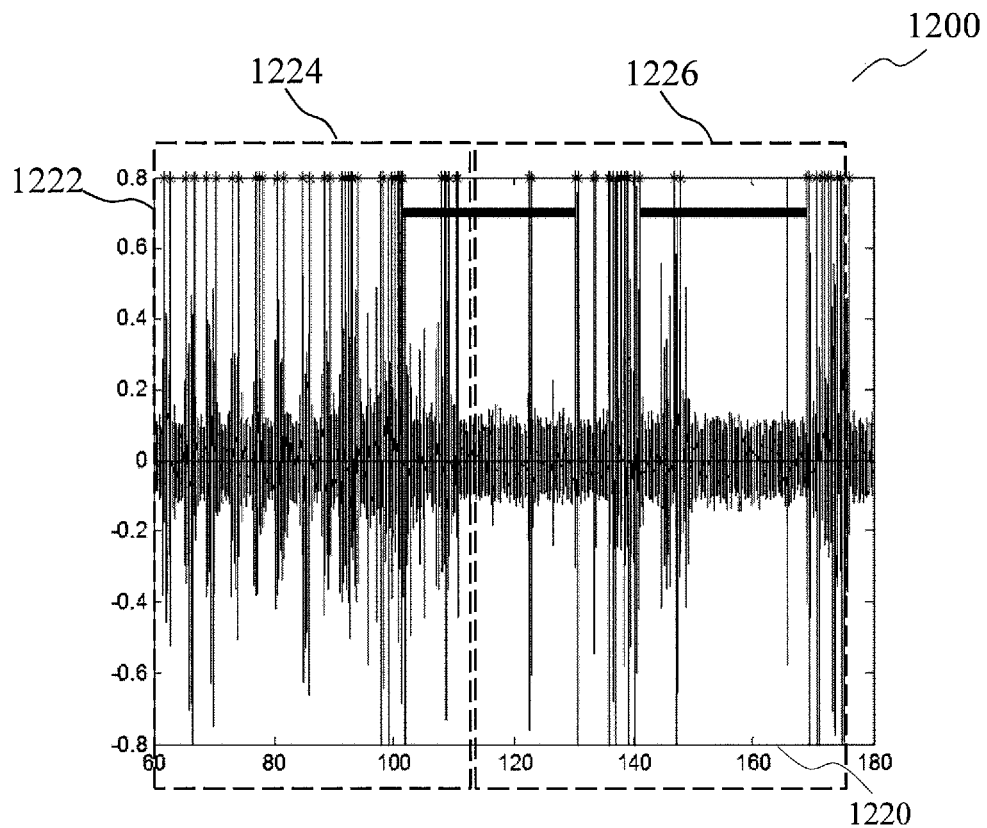
FIG. 12 shows an oscillogram of the breathing sounds of a subject with detected apnea.

FIG. 12 shows an oscillogram 1200 of the breathing sounds of a subject with detected apnea. The horizontal axis 1220 indicates time while the vertical axis 1222 indicates amplitude. The first half 1224 of the oscillogram 1200 shows both normal breathing sounds while the second half 1226 of the oscillogram 1200 shows the occurrence of apnea. The peaks and troughs of the sound wave correspond to inspirations and expirations. The gap between the peaks or troughs indicates a pause in the breath. The second half 1226 shows that the time gap between the peaks of the sound wave became almost five times the time gap between the peaks of the sound wave in the first half 1224. In other words, the subject was breathing normally until around t=110 s and from t=110 s, the subject exhibited apnea.

Figure 13:
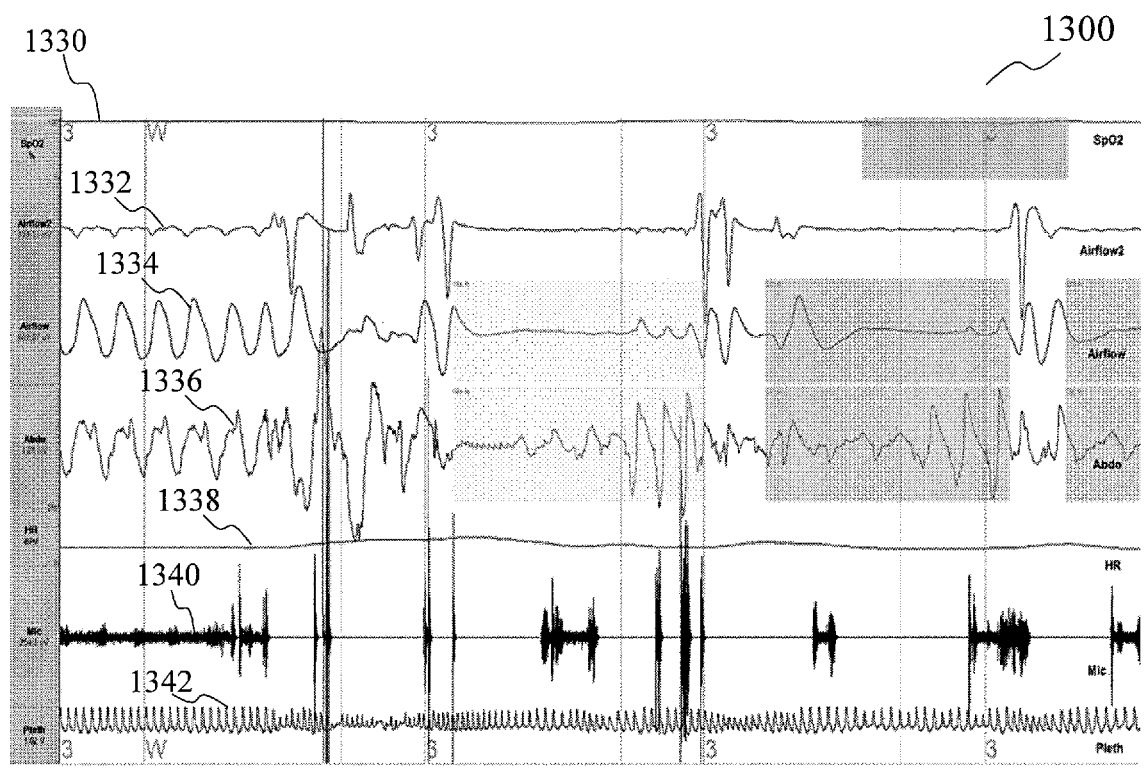
FIG. 13 shows the PSG recordings of the subject whose respiratory sounds were shown in the oscillogram of FIG. 12.

FIG. 13 shows the PSG recordings 1300 of the subject whose respiratory sounds were shown in the oscillogram of FIG. 12. The PSG recordings 1300 were made simultaneously with the oscillogram of FIG. 12. The subject exhibited both normal breathing and apnea during the recording. The PSG recordings 1300 includes a first graph 1330, a second graph 1332, a third graph 1334, a fourth graph 1336, a fifth graph 1338, a sixth graph 1340 and a seventh graph 1342. The first graph 1330 represents the finger oximeter readings. The second graph 1332 represents a first air flow rate through one from the group consisting of the subject's nostrils or mouth. The third graph 1334 represents a second air flow rate through the other one from the group consisting of the subject's nostrils or mouth. The fourth graph 1336 represents the readings from the belt on the subject's abdomen. The fifth graph 1338 represents the heart rate of the subject. The sixth graph 1340 represents the sound wave of the subject's breathing sounds. The seventh graph 1342 represents the plethysmography readings.

Figure 14:
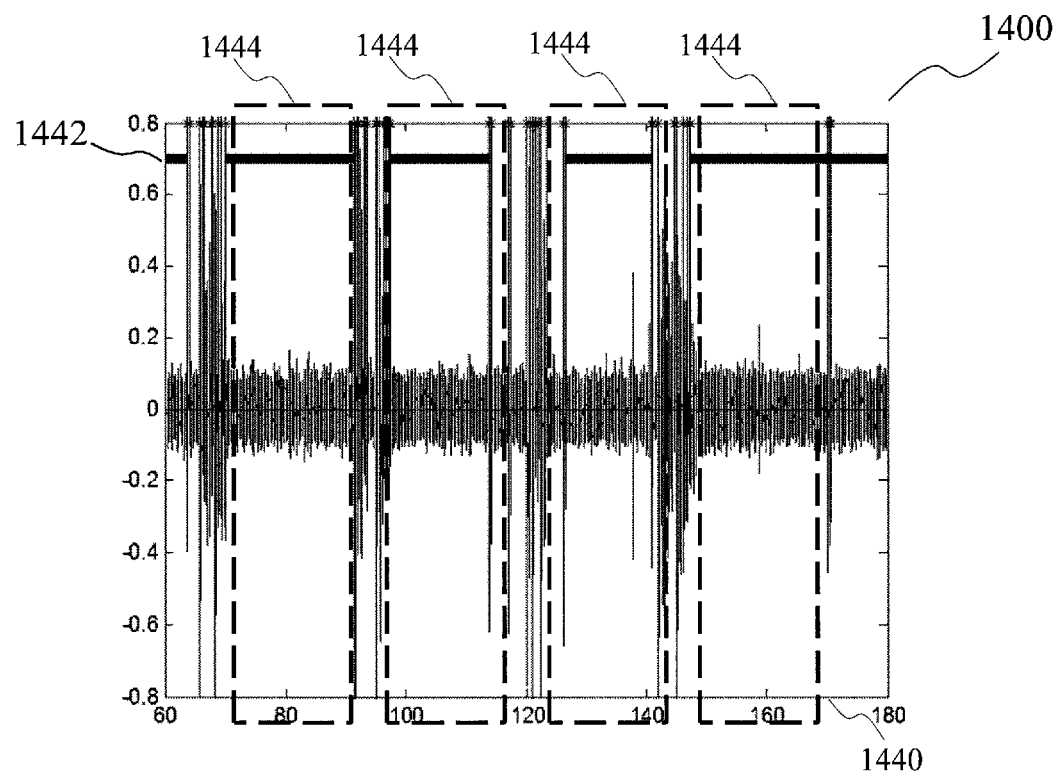
FIG. 14 shows an oscillogram of the breathing sounds of a subject with detected apnea.

FIG. 14 shows an oscillogram 1400 of the breathing sounds of a subject with detected apnea. The horizontal axis 1440 indicates time while the vertical axis 1442 indicates amplitude. The oscillogram 1400 shows the repeated occurrence of apnea at intervals 1444.

Figure 15:
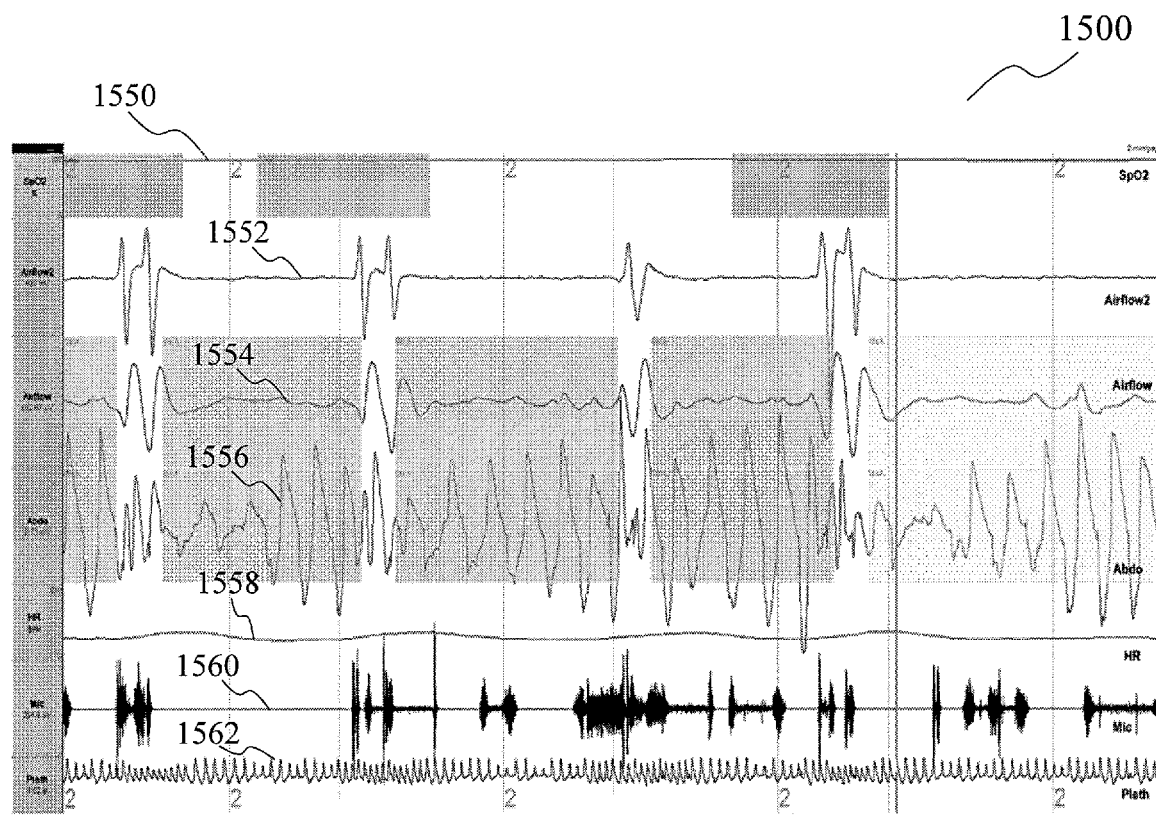
FIG. 15 shows the PSG recordings of the subject whose respiratory sounds were shown in the oscillogram of FIG. 14.

FIG. 15 shows the PSG recordings 1500 of the subject whose respiratory sounds were shown in the oscillogram of FIG. 14. The PSG recordings 1500 were made simultaneously with the oscillogram of FIG. 14. The subject exhibited repeated apnea during the recording. The PSG recordings 1500 includes a first graph 1550, a second graph 1552, a third graph 1554, a fourth graph 1556, a fifth graph 1558, a sixth graph 1560 and a seventh graph 1562. The first graph 1550 represents the finger oximeter readings. The second graph 1552 represents a first air flow rate through one from the group consisting of the subject's nostrils or mouth. The third graph 1554 represents a second air flow rate through the other one from the group consisting of the subject's nostrils or mouth. The fourth graph 1556 represents the readings from the belt on the subject's abdomen. The fifth graph 1558 represents the heart rate of the subject. The sixth graph 1560 represents the sound wave of the subject's breathing sounds. The seventh graph 1562 represents plethysmography readings.

Figure 16:
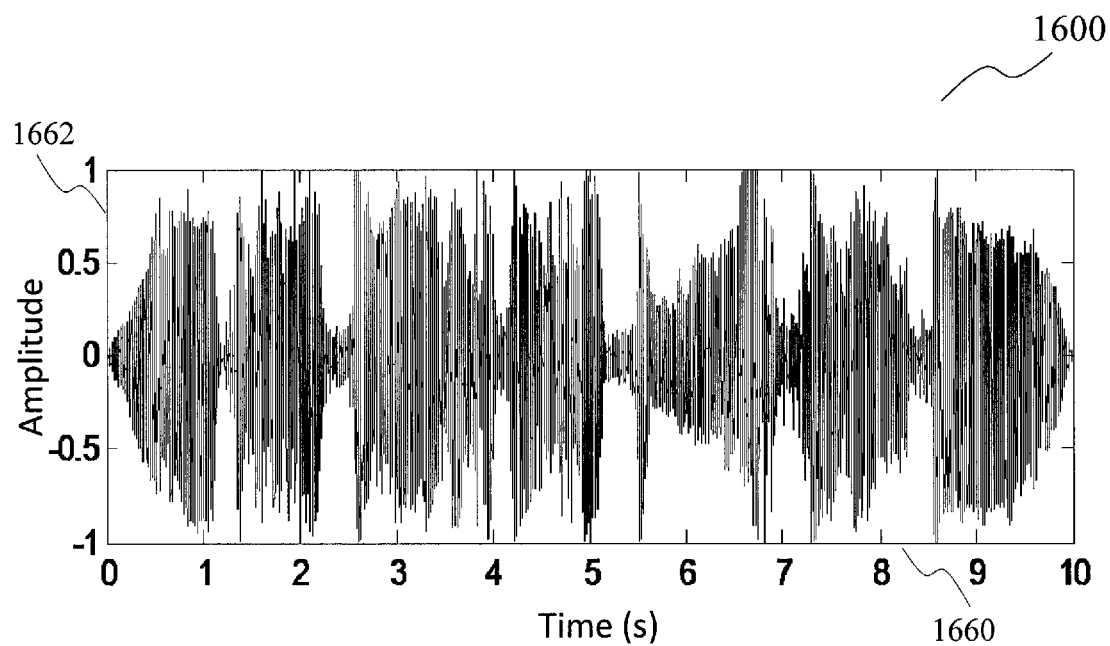
FIG. 16 shows the oscillogram of breathing sounds that indicate a complex and irregular breathing pattern.

FIG. 16 shows the oscillogram 1600 of breathing sounds that indicate a complex and irregular breathing pattern. The horizontal axis 1660 indicates time while the vertical axis 1662 indicates amplitude. The oscillogram 1600 shows the raw respiratory sound received from a subject. In other words, the oscillogram 1600 may show the audio output of the audio sensor 110, prior to any processing.

Figure 17:
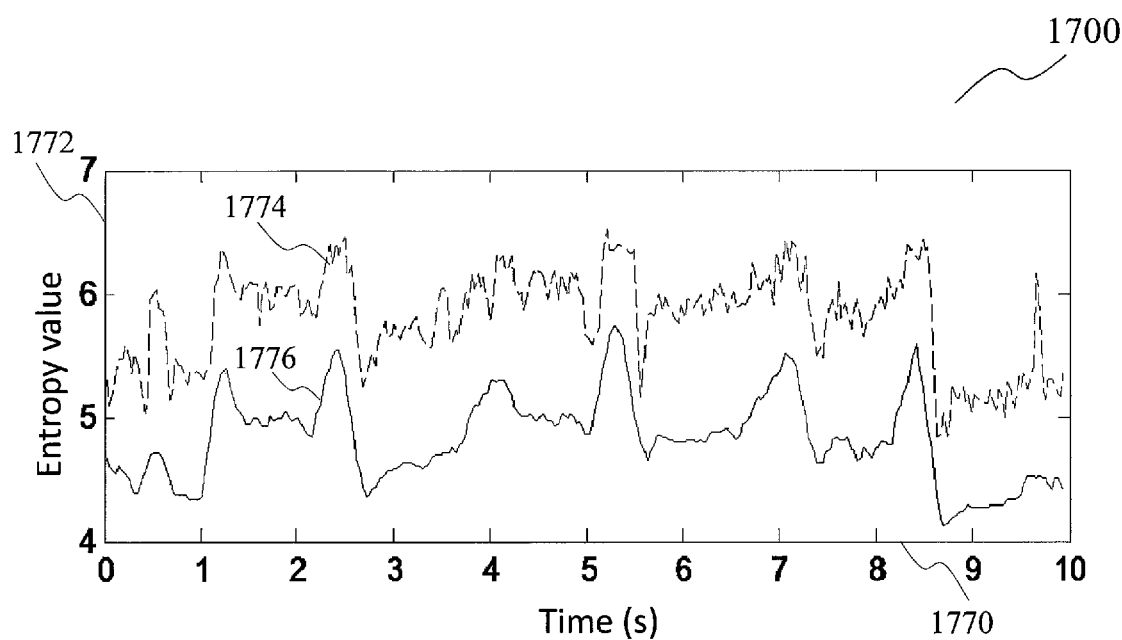
FIG. 17 shows a graph showing the entropy values of the audio signal shown in the oscillogram of FIG. 16.

FIG. 17 shows a graph 1700 showing the entropy values of the audio signal shown in the oscillogram 1600. The horizontal axis 1770 indicates time while the vertical axis 1772 indicates amplitude. The graph 1700 includes a first plot 1774 and a second plot 1776. The first plot 1774 which is shown as a dashed line, represents the entropy values of the audio signal. The breath analysis sub-module 774 may calculate the entropy values of the first plot 1774 based on the frequency components of the dominant component output 784, where less significant frequency components had been removed. The second plot 1776 which is shown as a solid line, represents the entropy values of the audio signal obtained using the enhanced entropy method. The breath analysis sub-module 774 may calculate the entropy values of the second plot 1776 based on the frequency components of an enhanced dominant component output. The subtraction sub-module 772 may replace the less significant frequency components with small values, instead of zero, to provide the enhanced dominant component output. The local maximum points in the second plot 1776 indicate the pauses between the inspiratory phases and the expiratory phases. The graph 1700 shows the respiratory phases more clearly, as compared to the graph 1600. The second plot 1776 also more clearly indicates the respiratory phases as compared to the first plot 1774. For example, a peak around 4 s in the second plot 1776 indicates the end of a respiratory phase. The second plot 1776 also provides a better description, in other words more clearly show the breathing pattern during 7-8.4 s where an unstable transit phase in the respiration is suppressed.

Figure 18:
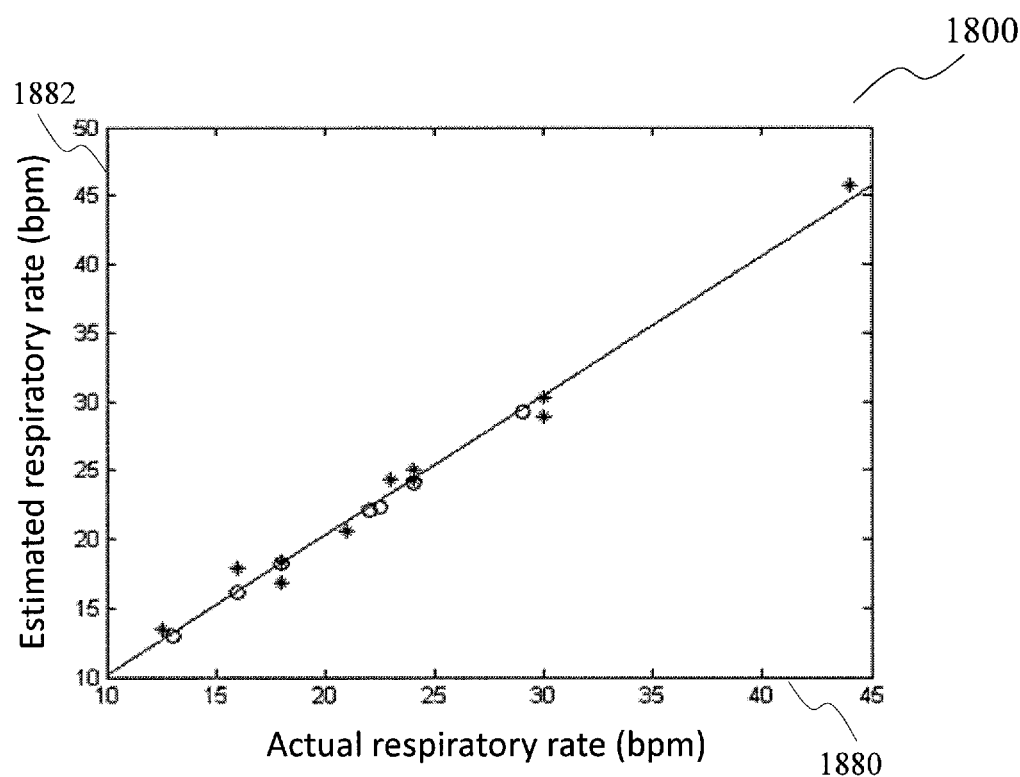
FIG. 18 shows a graph that shows the results of respiratory rate estimation when the method according to various embodiments is applied to open-source data.

FIG. 18 shows a graph 1800 that shows the results of respiratory rate estimation when the method according to various embodiments is applied to open-source data. The horizontal axis 1880 represents the actual respiratory rates obtained from open-source data while the vertical axis 1882 represents the respiratory rates estimated using the method according to various embodiments. The graph 1800 shows that there is a strong linear correlation between the results of the method and the reference respiratory rate.

Figures 19, 20:
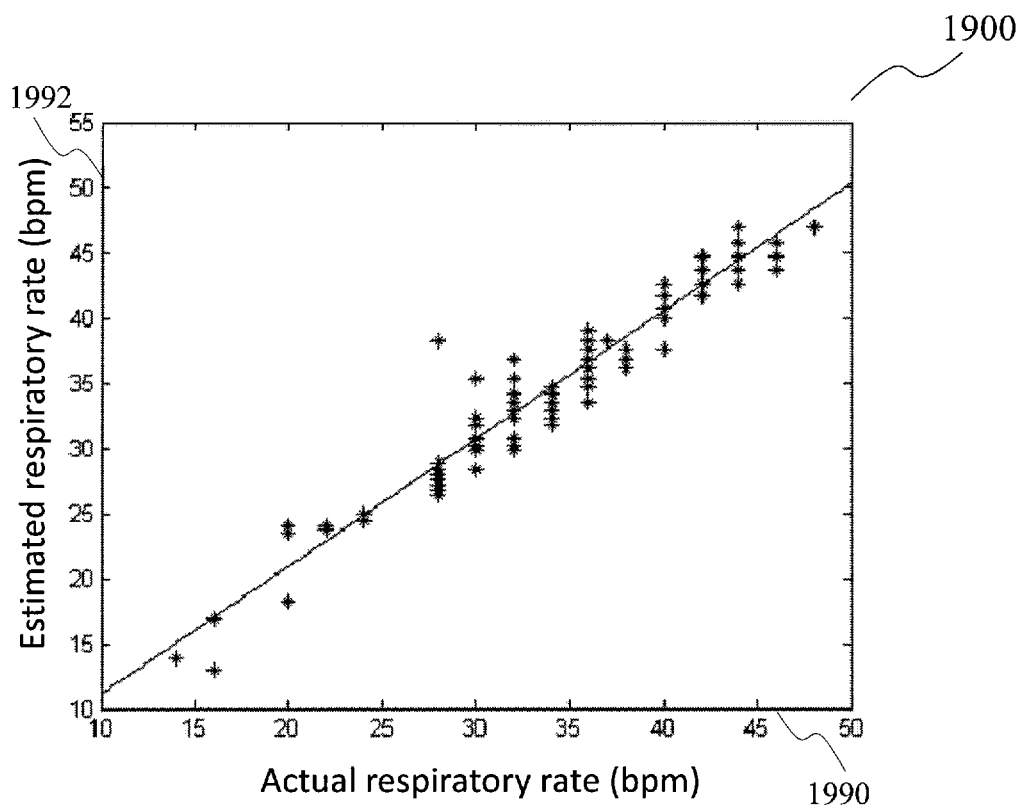
FIG. 19 show the results of respiratory rate estimation when the method according to various embodiments is applied to local hospital data.
FIG. 20 shows a comparison table that compares the detection results of the method according to various embodiments against the detection results of the PSG test, for several types of apnea events.

FIG. 19 shows a graph 1900 showing the results of respiratory rate estimation when the method according to various embodiments is applied to local hospital data. The horizontal axis 1990 represents the actual respiratory rates obtained from local hospital data while the vertical axis 1992 represents the respiratory rates estimated using the method according to various embodiments. The graph 1900 shows that there is a strong linear correlation between the results of the method and the reference respiratory rate.

FIG. 20 shows a table 2000 which compares the detection results of the method according to various embodiments against the detection results of the PSG test, for several types of apnea events. The first column 2034 lists the apnea events. The second column 2036 lists the PSG results, including the start time and duration of the detected apnea events. The third column 2038 lists the results of the method according to various embodiments, including the start time and duration of the detected apnea events. The first row 2020 lists the test results of a first mixed apnea event. The second row 2022 lists the test results of a second mixed apnea event. The third row 2024 lists the test results of a first obstructive apnea event. The fourth row 2026 lists the test results of a second obstructive apnea event. The fifth row 2028 lists the test results of a first hypopnea event. The sixth row 2030 lists the test results of a second hypopnea event. The seventh row 2032 lists the test results of a central apnea event. The results in the third column 2038 at least substantially correspond to the results in the second column 2036.

Figure 21:
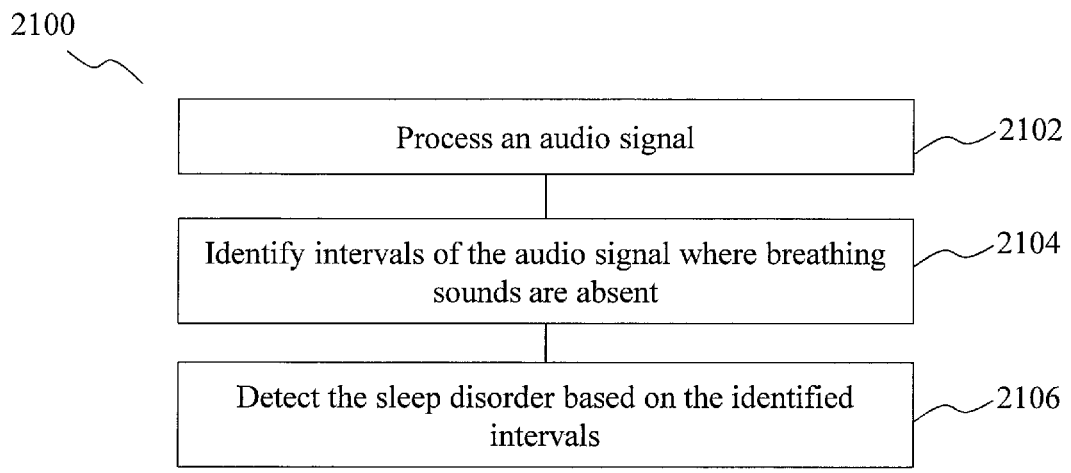
FIG. 21 shows a flow diagram of a method for detecting a sleep disorder according to various embodiments.

FIG. 21 shows a flow diagram 2100 of a method for detecting a sleep disorder according to various embodiments. The method may include a plurality of processes. In 2102, an audio signal may be processed. The audio signal may include breathing sounds made by a subject when the subject is asleep. The processing of the audio signal in 2102 may include at least one of the filtering and amplification carried out by the sensor circuit 224 or the pre-processing carried out by the pre-processing module 550. The processing of the audio signal may also include processing carried out by sub-modules of the detection module 552, for example, the STFT carried out by the STFT sub-module 770 and the baseline subtraction carried out by the subtraction sub-module 772. In 2104, intervals of the audio signal where breathing sounds are absent may be identified. The identified intervals may also be referred herein as silent intervals. The identification of silent intervals may be carried out by the detection module 552. The process of identifying the silent intervals may include the processes carried out by the interval detection sub-module 778. In 2106, the sleep disorder may be detected based on the identified intervals. The process of detecting the sleep disorder may include processes carried out by the identification module 556 and may also include the processes carried out by the feature module 554.

In other words, according to various embodiments, the method for detecting a sleep disorder may include processing an audio signal to identify silent intervals in the audio signal. The audio signal may be an electrical signal representing the sound waves made by a subject when the subject is asleep. The audio signal may include information on the breathing sounds of the subject. The silent intervals may be intervals in the audio signal where breathing sounds are absent. The method may include estimating background noise in the audio signal, which may be carried out in the noise estimation sub-module 776. To estimate the background noise, at least one of pauses within each identified breathing cycle or pauses between successive identified breathing cycles may first be identified, so that power levels of the segments of the audio signal corresponding to the pauses may be determined. The background noise may be estimated based on the power levels of the segments of the audio signal corresponding to the pauses. The breathing cycles may be identified by computing entropy values of frequency components of the audio signal and identifying at least substantially periodic characteristics of the audio signal based on the computer entropy values. The breathing cycles may be identified by the breath analysis sub-module 774. The at least substantially periodic characteristics of the audio signal may be identified by autocorrelating the computed entropy values. The entropy values may be computed on frequency components of the audio signal that have a power level above an average power level of the audio signal. The computation of the entropy values may be carried out by the breath analysis sub-module 774. The subtraction sub-module 772 may identify the frequency components that have a power level above the average power level of the audio signal. The method may further include identifying the absence of breathing sounds based on power levels of the audio signal and the estimated background noise. The identification of the absence of breathing sounds may be carried out by the interval detection sub-module 778. The identified silent intervals may be classified as abnormality events, also referred herein as candidate events, based on durations of the identified intervals and a predetermined threshold, also referred herein as a duration threshold. The classification of the identified silent intervals may be carried out by the candidate detection sub-module 780. The method may further include detecting the sleep disorder based on the silent intervals. Detecting the sleep disorder may include computing a vector of features to represent each abnormality event, and may further include determining whether the abnormality events are indicative of the sleep disorder. A vector of features representing each abnormality event may be computed by the feature extraction sub-module 990. The vector of features may be one of MFCC, linear prediction coefficients, perceptual linear prediction coefficients or wavelet transform coefficients. A classifier based on one of Bayes networks, decision trees, k-means clustering, kth-nearest neighbour, multivariate discriminant analysis, support vector machines, neural networks or ELM, may be used to determine whether the abnormality events are indicative of the sleep disorder based on the identified silent intervals and the vector of features. The classifier may be identical to, or similar to the classifier sub-module 1012. The method may be used clinically to detect, diagnose or make a prognosis on the subject's sleep disorder condition. The method may also be used in respiratory-based healthcare monitoring applications, for example to evaluate the effectiveness of medication on the subject.

Figure 22:
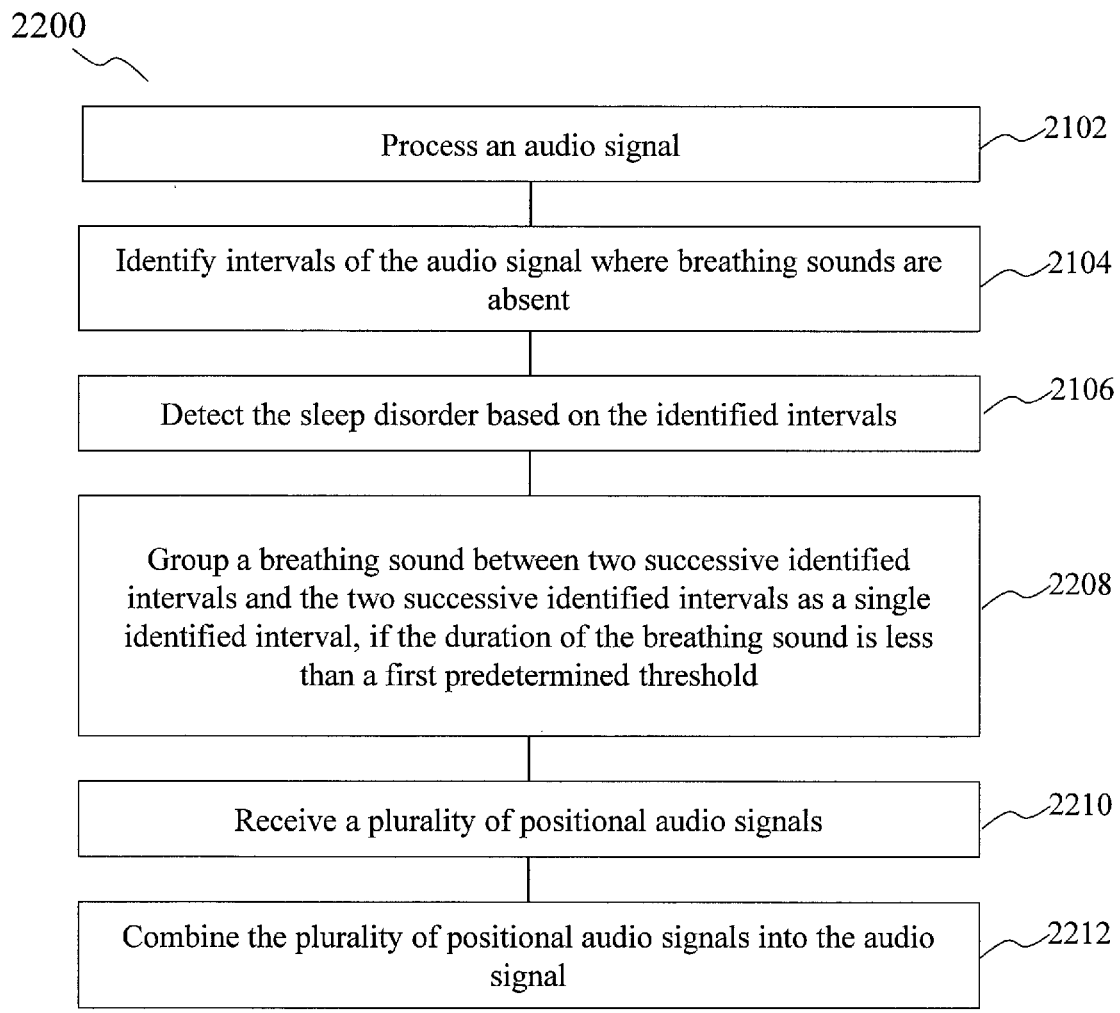
FIG. 22 shows a flow diagram of a method for detecting a sleep disorder according to various embodiments.

FIG. 22 shows a flow diagram 2200 of a method for detecting a sleep disorder according to various embodiments. In addition to the processes of the method shown in the flow diagram 2100, the method of flow diagram 2200 may further include process 2208, in which the breathing sound between two successive identified intervals and the two successive identified intervals may be grouped as a single identified interval, if the duration of the breathing sound is less than a first predetermined threshold. The grouping process in 2208 may be carried out by the grouping sub-module 1010. The method of flow diagram 2200 may further include 2210, in which a plurality of positional audio signals may be received. Each positional audio signal may be received from a respective acoustic sensor of a plurality of acoustic sensors. The acoustic sensors may be identical to, or similar to, the audio sensors 110. Each acoustic sensor may be positioned at a respective location of a plurality of locations. The method may further include 2212, in which the plurality of positional audio signals may be combined into the audio signal. The process of combining the plurality of positional audio signals into the audio signal may be carried out by the signal combining module 330. Interfering sounds may be removed when the plurality of positional audio signals are combined into the audio signal.

Figure 23:
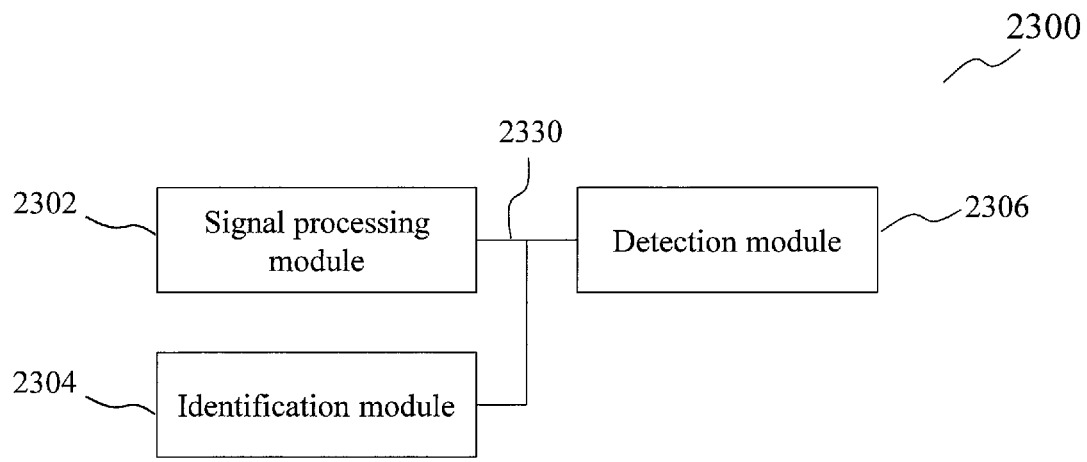
FIG. 23 shows a conceptual diagram of a sleep disorder detection device according to various embodiments.

FIG. 23 shows a conceptual diagram of a sleep disorder detection device 2300 according to various embodiments. The sleep disorder detection device 2300 may include a signal processing module 2302, an identification module 2304 and a detection module 2306. The signal processing module 2302 may be configured to process an audio signal including breathing sounds made by a subject when the subject is asleep. The signal processing module 2302 may include at least one of the sensor circuit 224, the STFT sub-module 770 or the subtraction sub-module 772. The identification module 2304 may be configured to identify intervals of the audio signal where breathing sounds are absent. The identification module 2304 may include the interval detection sub-module 778, and may further include at least one of the breath analysis sub-module 774, the candidate detection sub-module 780 or the noise estimation sub-module 776. The detection module 2306 may be configured to detect the sleep disorder based on the identified intervals. The detection module 2306 may include the identification module 556 and may further include at least one of the feature module 554 or the candidate detection sub-module 780. The signal processing module 2302, the identification module 2304 and the detection module 2306 may be coupled with each other, like indicated by lines 2330, for example electrically coupled, for example using a line or a cable, and/or mechanically coupled.

Figure 24:
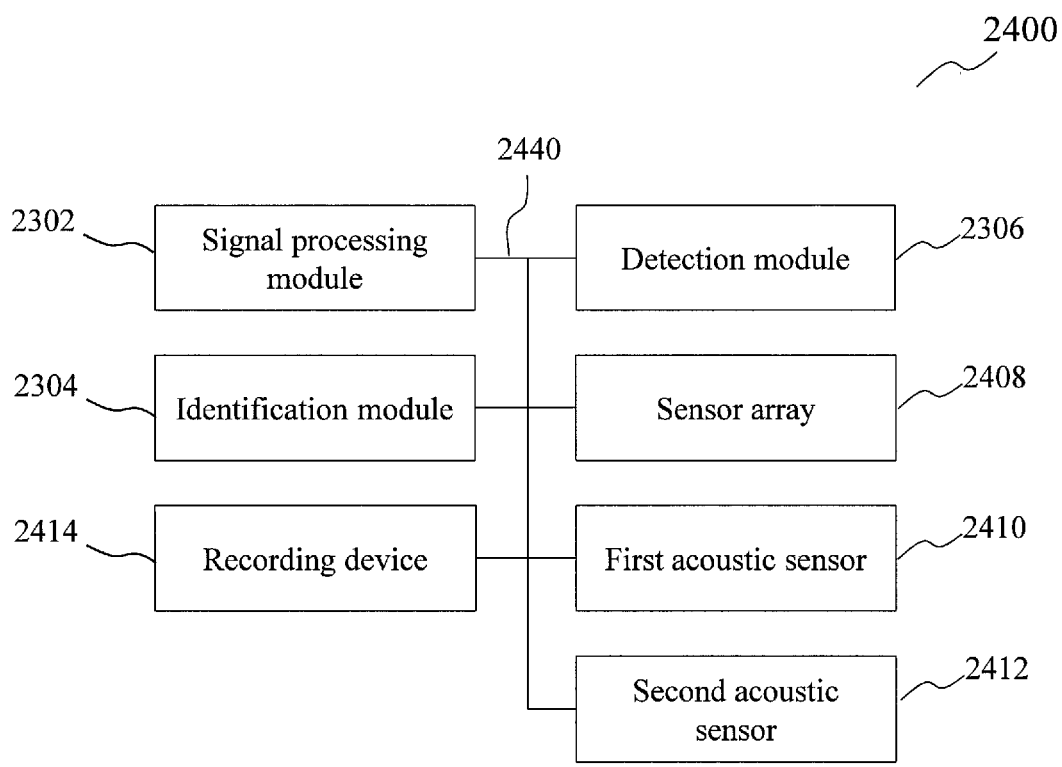
FIG. 24 shows a conceptual diagram of a sleep disorder detection device according to various embodiments.

FIG. 24 shows a conceptual diagram of a sleep disorder detection device 2400 according to various embodiments. The sleep disorder detection device 2400 may be similar to the sleep disorder detection device 2400 in that it may also include a signal processing module 2302, an identification module 2304 and a detection module 2306. The sleep disorder detection device 2400 may further include a first acoustic sensor 2410 and a second acoustic sensor 2412. At least one of the first acoustic sensor 2410 or the second acoustic sensor 2412 may be one of a microphone or a stethoscope. The first acoustic sensor 2410 may be configured to receive the audio signal. The second acoustic sensor 2412 may be configured to receive background noise. Each of the first acoustic sensor 2410 and the second acoustic sensor 2412 may include the audio sensor 110. The signal processing module 2302 may be further configured to suppress interference noise in the audio signal based on the received background noise. The sleep disorder detection device 2400 may further include a sensor array 2408. The sensor array 2408 may be configured to amplify a first audio signal received from a direction of the subject and may be further configured to suppress a second audio signal received from other directions. The sensor array 2408 may include the first acoustic sensor 2410 and the second acoustic sensor 2412. The sensor array 2408 may include the SES 222. The first audio signal may be the audio signal. The second audio signal may be the background noise. The sleep disorder detection device 2400 may further include a recording device 2414. The recording device 2414 may include the storage sub-system 236. The recording device 2414 may be configured to record the audio signal. The sleep disorder detection device 2400 may be a wearable device. The signal processing module 2302, the identification module 2304, the detection module 2306, the sensor array 2408, the first acoustic sensor 2410, the second acoustic sensor 2412 and the recording device 2414 may be coupled with each other, like indicated by lines 2440, for example electrically coupled, for example using a line or a cable, and/or mechanically coupled.

The following examples pertain to further embodiments.

Example 1 is a method for detecting a sleep disorder, the method including: processing an audio signal, the audio signal including breathing sounds made by a subject when the subject is asleep; identifying intervals of the audio signal where breathing sounds are absent; and detecting the sleep disorder based on the identified intervals.

In example 2, the subject-matter of example 1 can optionally include that identifying intervals of the audio signal where breathing sounds are absent includes estimating background noise in the audio signal, and identifying an absence of breathing sounds based on power levels of the audio signal and the estimated background noise.

In example 3, the subject-matter of example 2 can optionally include that estimating the background noise includes identifying breathing cycles, and estimating the background noise based on power levels of segments of the audio signal corresponding to at least one of pauses within each identified breathing cycle or pauses between successive identified breathing cycles.

In example 4, the subject-matter of example 3 can optionally include that identifying the breathing cycles includes computing entropy values of frequency components of the audio signal, and identifying at least substantially periodic characteristics of the audio signal based on the computed entropy values.

In example 5, the subject-matter of example 4 can optionally include that computing entropy values of frequency components of the audio signal includes extracting frequency components having a power level above an average power level of the audio signal, and computing entropy values of the extracted frequency components.

In example 6, the subject-matter of examples 4 or 5 can optionally include that identifying at least substantially periodic characteristics of the audio signal includes auto-correlating the computed entropy values.

In example 7, the subject-matter of any one of examples 1 to 6 can optionally include grouping a breathing sound between two successive identified intervals and the two successive identified intervals as a single identified interval, if the duration of the breathing sound is less than a first predetermined threshold.

In example 8, the subject-matter of any one of examples 1 to 7 can optionally include that detecting the sleep disorder includes classifying the identified intervals as abnormality events, based on durations of the identified intervals and a second predetermined threshold.

In example 9, the subject-matter of example 8 can optionally include that detecting the sleep disorder further includes computing a vector of features to represent each abnormality event and determining whether the abnormality events are indicative of the sleep disorder based on the identified intervals and the computed vector of features, using a classifier.

In example 10, the subject-matter of example 9 can optionally include that the vector of features is one of mel-frequency cepstral coefficients, linear prediction coefficients, perceptual linear prediction coefficients or wavelet transform coefficients.

In example 11, the subject-matter of examples 9 or 10 can optionally include that the classifier includes one of Bayes networks, decisions trees, k-means clustering, kth-nearest neighbour, multivariate discriminant analysis, support vector machines, neural networks or Extreme Learning Machine.

In example 12, the subject-matter of any one of examples 1 to 11 can optionally include receiving a plurality of positional audio signals, wherein each positional audio signal of the plurality of positional audio signals is received from a respective acoustic sensor of a plurality of acoustic sensors; and combining the plurality of positional audio signals into the audio signal.

In example 13, the subject-matter of example 12 can optionally include that each positional audio signal is received from a respective location of a plurality of locations.

In example 14, the subject-matter of examples 12 or 13 can optionally include that combining the plurality of positional audio signals into the audio signal includes removing interfering sounds.

Example 15 is a sleep disorder detection device including: a signal processing module configured to process an audio signal including breathing sounds made by a subject when the subject is asleep; an identification module configured to identify intervals of the audio signal where breathing sounds are absent; and a detection module configured to detect the sleep disorder based on the identified intervals.

In example 16, the subject-matter of example 15 can optionally include a first acoustic sensor configured to receive the audio signal; and a second acoustic sensor configured to receive background noise.

In example 17, the subject-matter of example 16 can optionally include that the signal processing module is further configured to suppress interference noise in the audio signal based on the received background noise.

In example 18, the subject-matter of any one of examples 15 to 17 can optionally include a sensor array configured to amplify a first audio signal received from a direction of the subject and further configured to suppress a second audio signal received from other directions.

In example 19, the subject-matter of any one of examples 16 to 18 can optionally include that at least one of the first acoustic sensor or the second acoustic sensor is one of a microphone or a stethoscope.

In example 20, the subject-matter of any one of examples 15 to 19 can optionally include that the sleep disorder detection device is a wearable device.

In example 21, the subject-matter of any one of examples 15 to 20 can optionally include a recording device configured to record the audio signal.

While embodiments of the invention have been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced. It will be appreciated that common numerals, used in the relevant drawings, refer to components that serve a similar or the same purpose.

The invention claimed is:

1. A method for detecting a sleep disorder, the method comprising:
    processing an audio signal, the audio signal comprising breathing sounds made by a subject when the subject is asleep;
    identifying intervals of the audio signal where breathing sounds are absent;
    determining a duration of a breathing sound between two successive identified intervals;
    grouping the breathing sound and the two successive identified intervals as a single identified interval, based on comparing the determined duration of the breathing sound with a first predetermined threshold; and
    detecting the sleep disorder based on the identified intervals.

2. The method of claim 1, wherein identifying intervals of the audio signal where breathing sounds are absent comprises estimating background noise in the audio signal, and identifying an absence of breathing sounds based on power levels of the audio signal and the estimated background noise.

3. The method of claim 2, wherein estimating the background noise comprises identifying breathing cycles, and estimating the background noise based on power levels of segments of the audio signal corresponding to at least one of pauses within each identified breathing cycle or pauses between successive identified breathing cycles.

4. The method of claim 3, wherein identifying the breathing cycles comprises computing entropy values of frequency components of the audio signal, and identifying at least substantially periodic characteristics of the audio signal based on the computed entropy values.

5. The method of claim 4, wherein computing entropy values of frequency components of the audio signal comprises extracting frequency components having a power level above an average power level of the audio signal, and computing entropy values of the extracted frequency components.

6. The method of claim 4, wherein identifying at least substantially periodic characteristics of the audio signal comprises autocorrelating the computed entropy values.

7. The method of claim 1, wherein detecting the sleep disorder comprises classifying the identified intervals as abnormality events, based on durations of the identified intervals and a second predetermined threshold.

8. The method of claim 7, wherein detecting the sleep disorder further comprises computing a vector of features to represent each abnormality event and determining whether the abnormality events are indicative of the sleep disorder based on the identified intervals and the computed vector of features, using a classifier.

9. The method of claim 8, wherein the vector of features is one of mel-frequency cepstral coefficients, linear prediction coefficients, perceptual linear prediction coefficients or wavelet transform coefficients.

10. The method of claim 8, wherein the classifier comprises one of Bayes networks, decisions trees, k-means clustering, kth-nearest neighbour, multivariate discriminant analysis, support vector machines, neural networks or Extreme Learning Machine.

11. The method of claim 1, further comprising:
    receiving a plurality of positional audio signals, wherein each positional audio signal of the plurality of positional audio signals is received from a respective acoustic sensor of a plurality of acoustic sensors; and
    combining the plurality of positional audio signals into the audio signal.

12. The method of claim 11, wherein each positional audio signal is received from a respective location of a plurality of locations.

13. The method of claim 11, wherein combining the plurality of positional audio signals into the audio signal comprises removing interfering sounds.

14. A sleep disorder detection device comprising:
    a signal processing module configured to process an audio signal comprising breathing sounds made by a subject when the subject is asleep;
    an identification module configured to identify intervals of the audio signal where breathing sounds are absent,
    wherein the identification module is further configured to determine a duration of a breathing sound between two successive identified intervals,
    wherein the identification module is further configured to group the breathing sound and the two successive identified intervals as a single identified interval, based on comparing the determined duration of the breathing sound with a predetermined threshold; and
    a detection module configured to detect the sleep disorder based on the identified intervals.

15. The sleep disorder detection device of claim 14, further comprising:
    a first acoustic sensor configured to receive the audio signal; and
    a second acoustic sensor configured to receive background noise.

16. The sleep disorder detection device of claim 15, wherein the signal processing module is further configured to suppress interference noise in the audio signal based on the received background noise.

17. The sleep disorder detection device of claim 14, further comprising:
    a sensor array configured to amplify a first audio signal received from a direction of the subject and further configured to suppress a second audio signal received from other directions.

18. The sleep disorder detection device of claim 15, wherein at least one of the first acoustic sensor or the second acoustic sensor is one of a microphone or a stethoscope.

19. The sleep disorder detection device of claim 14, wherein the sleep disorder detection device is a wearable device.

\* \* \* \* \*